(12) United States Patent
Stoessel

(10) Patent No.: US 8,617,723 B2
(45) Date of Patent: Dec. 31, 2013

(54) METAL COMPLEXES

(75) Inventor: Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 428 days.

(21) Appl. No.: 12/934,487

(22) PCT Filed: Mar. 4, 2009

(86) PCT No.: PCT/EP2009/001516
§ 371 (c)(1),
(2), (4) Date: Sep. 24, 2010

(87) PCT Pub. No.: WO2009/118087
PCT Pub. Date: Oct. 1, 2009

(65) Prior Publication Data
US 2011/0012100 A1 Jan. 20, 2011

(30) Foreign Application Priority Data

Mar. 25, 2008 (DE) .......................... 10 2008 015 526

(51) Int. Cl.
*H01L 51/54* (2006.01)
*C09K 11/06* (2006.01)
(52) U.S. Cl.
USPC ........... 428/690; 428/917; 313/504; 313/506; 252/301.16; 257/40; 257/102; 257/E51.041; 257/E51.043; 257/E51.044
(58) Field of Classification Search
None
See application file for complete search history.

(56) References Cited

U.S. PATENT DOCUMENTS

| | | | |
|---|---|---|---|
| 2001/0019782 A1* | 9/2001 | Igarashi et al. | 428/690 |
| 2003/0054198 A1* | 3/2003 | Tsuboyama et al. | 428/690 |
| 2005/0170207 A1* | 8/2005 | Ma et al. | 428/690 |
| 2008/0027220 A1 | 1/2008 | Stossel et al. | |
| 2009/0292080 A1 | 11/2009 | Stossel et al. | |

FOREIGN PATENT DOCUMENTS

| | | |
|---|---|---|
| EP | 1211257 A2 | 6/2002 |
| WO | WO-2006/008069 A1 | 1/2006 |
| WO | WO-2006/061182 A1 | 6/2006 |
| WO | WO-2007/011696 A2 | 1/2007 |
| WO | WO-2009/038685 A1 | 3/2009 |

OTHER PUBLICATIONS

Koshevoy, I., et al., "Synthesis of a new C3-cymmetric legend and its transition metal complexes with helicoidal chirality," 22nd International Conference on Organometallic Chemistry ICOMC, 2006, vol. 2, P45, p. 233.

Seel, C., et al., "Molecules with large cavities in supramolecular chemistry," Angewandte Chemie Int. Ed. Engl., 1992, vol. 31, No. 5. pp. 528-549.

* cited by examiner

*Primary Examiner* — Michael H Wilson
(74) *Attorney, Agent, or Firm* — Novak Druce Connolly Bove + Quigg LLP

(57) ABSTRACT

The present invention relates to metal complexes of the formula (1) and to the use thereof in organic electroluminescent devices, and to organic electroluminescent devices which comprise these metal complexes.

15 Claims, No Drawings

METAL COMPLEXES

CROSS-REFERENCE TO RELATED APPLICATIONS

This application is a national stage application (under 35 U.S.C. §371) of PCT/EP2009/001516, filed Mar. 4, 2009, which claims benefit of German application 10 2008015 526.8, filed Mar. 25, 2008.

BACKGROUND OF THE INVENTION

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. In recent years, the emitting materials employed are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in OLEDs which exhibit triplet emission. Thus, the physical properties of phosphorescent OLEDs are still inadequate with respect to efficiency, operating voltage and lifetime for use of triplet emitters in high-quality and long-lived electroluminescent devices. This applies, in particular, to OLEDs which emit in the relatively short-wave range, i.e. green and in particular blue. Thus, no blue-emitting triplet emitters which meet the technical requirements for industrial use are known to date.

In accordance with the prior art, the triplet emitters employed in phosphorescent OLEDs are, in particular, iridium complexes. An improvement in these OLEDs has been achieved by employing metal complexes with polypodal ligands or cryptates, as a consequence of which the complexes have higher thermal stability, which results in a longer lifetime of the OLEDs (WO 04/081017, WO 05/113563, WO 06/008069). However, these complexes are not suitable for blue emission, in particular for saturated deep-blue emission.

BRIEF SUMMARY OF THE INVENTION

The object of the present invention is therefore to provide novel metal complexes which are suitable as emitters or also as matrix materials or in other functions for use in OLEDs. In particular, the object is to provide emitters and matrix materials which are suitable for blue-phosphorescing OLEDs.

Surprisingly, it has been found that certain metal chelate complexes described in greater detail below achieve this object and result in significant improvements in the organic electroluminescent device, in particular with respect to the lifetime, the efficiency and the stability to heating. This applies, in particular, to blue-phosphorescing electroluminescent devices. The present invention therefore relates to these metal complexes and to organic electroluminescent devices which comprise these complexes.

The present invention thus relates to compounds of the formula (1)

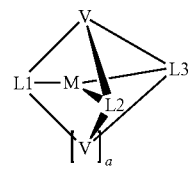

formula (1)

containing a metal M coordinated to a ligand L of the formula (2)

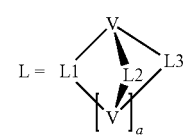

formula (2)

where the following applies to the symbols and indices used:

V is a bridging unit containing 1 to 80 atoms from the third, fourth, fifth and/or sixth main group, which covalently bonds the ligand moieties L1, L2 and L3 to one another;
a is 0 or 1, where, in the case where a=0, the bridging unit V is not present;
L1 is a ligand moiety of the formula (3)

formula (3)

$$\begin{array}{c} Cy1 \\ | \\ Z \\ | \\ Cy2 \end{array}$$

L2, L3 are, identically or differently on each occurrence, each a ligand moiety of the formula (3), formula (4) or formula (5)

formula (3)

$$\begin{array}{c} Cy1 \\ | \\ Z \\ | \\ Cy2 \end{array}$$

formula (4)

$$\begin{array}{c} Cy1 \\ | \\ Cy2 \end{array}$$

formula (5)

$$\begin{array}{c} D1 \\ | \\ D2 \end{array}$$

Cy1, Cy2 are, identically or differently on each occurrence, substituted or unsubstituted cyclic groups, which each contain at least one donor atom or a C atom in the ring or an exocyclic donor atom via which the cyclic group is bonded to the metal M; the groups Cy1 and Cy2 in formula (3) are connected to one another via the group Z and may additionally be linked to one another via substituents; the groups Cy1 and Cy2 in formula (4) are connected to one another via a single bond and may additionally be linked to one another via substituents;

Z is, identically or differently on each occurrence, a substituted or unsubstituted atom from the third, fourth, fifth or sixth main group which bridges the rings Cy1 and Cy2;

D1, D2 are identical or different on each occurrence and stand for a chemical group which contains at least one donor atom.

DETAILED DESCRIPTION OF THE INVENTION

For the purposes of the present invention, a ligand moiety is taken to mean the groups L1, L2 and L3 in the ligand of the formula (2), i.e. in each case the individual arms of the polypodal ligand or the bridges of the cryptand, which in each case coordinate to the metal and are linked via the bridge-head V.

For the purposes of the present invention, a donor atom is taken to mean atoms which have at least one free electron pair and are thus capable of bonding to a metal atom or metal ion. The donor atoms here may be neutral or negatively charged.

For the purposes of this invention, an exocyclic donor atom is taken to mean a donor atom which is not part of the cyclic group Cy1 or Cy2, but instead is bonded as substituent to Cy1 or Cy2 and has at least one free electron pair and is thus capable of bonding to a metal atom. Examples of exocyclic donor atoms are oxygen in the form of a phenolate, sulfur in the form of a thiolate or nitrogen in the form of an amine, imine, amide or imide.

If, in addition to a direct bond, the groups Cy1 and Cy2 are additionally linked to one another via substituents, this link may be aliphatic or unsaturated. An unsaturated link may be, for example, a —CR=CR— bridge.

The metal complexes of the formula (1) can be complexes of polypodal ligands or cryptates, irrespective of whether one bridging unit V (i.e. a=0) or two bridging units V (i.e. a=1) are present. For the purposes of this invention, a polypodal ligand is taken to mean a ligand in which three coordinating arms (ligand moieties) L1, L2 and L3 are bonded to one another by a group V. For the purposes of this invention, a cryptate is taken to mean a compound between a cryptand and a metal ion in which the metal ion is surrounded three-dimensionally by the bridges of the complex-forming cryptand. For the purposes of this invention, a cryptand is taken to mean a macropolycyclic ligand, in particular a ligand in which two bridge-head atoms or bridgehead groups V are connected by three bridges (ligand moieties) L1, L2 and L3, each of which is capable of coordinating to a metal atom.

The cyclic groups Cy1 and Cy2, which may be homocycles or hetero-cycles, may be saturated, unsaturated or aromatic or heteroaromatic. The groups are preferably aromatic or heteroaromatic or a cyclic, saturated or unsaturated carbene.

Preference is given to compounds of the formula (1) according to the invention, characterised in that they are uncharged, i.e. are electrically neutral. This is achieved in a simple manner in that the charges of the ligand moieties L1, L2 and L3 and of the bridging units V are selected so that they compensate for the charge of the complexed metal ion.

Preference is furthermore given to compounds of the formula (1) according to the invention, characterised in that the sum of the valence electrons around the metal atom is 18. This preference is due to the particular stability of these metal complexes (see, for example, Elschenbroich, Salzer, *Organometallchemie* [Organometallic Chemistry], Teubner Studienbükher, Stuttgart 1993).

Preference is furthermore given to compounds of the formula (1) according to the invention, characterised in that Cy1 is not equal to Cy2. In this case, it is preferred for one of the two rings to bonded via a metal-carbon bond, where the carbon formally has a negative charge, or via an exocyclic donor atom, which formally has a negative charge, preferably oxygen, sulfur or nitrogen, and for the other to be bonded via a neutral donor atom, which is carbon in the form of a carbene or is not equal to carbon and may either be part of the ring or an exocyclic substituent. Preferred neutral donor atoms not equal to carbon are nitrogen or phosphorus, in particular nitrogen. A formally negative charge of the coordinating atom is taken to mean that this would have a negative charge if the ligand were to be considered without the coordinated metal ion.

Preference is given to compounds of the formula (1) according to the invention, characterised in that the bridging unit V contains 1 to 80 atoms from the third, fourth, fifth and/or sixth main group (group 13, 14, 15 or 16 in accordance with IUPAC) or a 3- to 6-membered homo or heterocycle. These form the skeleton of the bridging unit. The bridging unit V here may also have an asymmetrical structure, i.e. the link from V to L1, L2 and L3 need not be identical. The bridging unit V may be neutral, singly, doubly or triply negatively charged or singly, doubly or triply positively charged. V is preferably neutral or singly negatively charged or singly positively charged. The charge of V is preferably selected here so that a neutral complex arises. Thus, for example, one or two neutral bridging units V are preferred if a trivalent metal ion $M^{3+}$ and three singly negative ligand moieties L1, L2 and L3 are involved. Furthermore, a singly negative bridging unit V and optionally a further neutral unit V are preferred if a tetravalent metal ion $M^{4+}$ and three singly negative ligand moieties L1, L2 and L3 are involved. Furthermore, two singly negative bridging units V are preferred if a pentavalent metal ion $M^{5+}$ and three singly negative ligand moieties L1, L2 and L3 are involved. Furthermore, a singly positive bridging unit V and optionally a further neutral unit V are preferred if a divalent metal ion $M^{2+}$ and three singly negative ligand moieties L1, L2 and L3 are involved. Furthermore, two singly positive bridging units V are preferred if a monovalent metal ion $M^+$ and three singly negative ligand moieties L1, L2 and L3 are involved.

Preference is given to compounds of the formula (1) according to the invention, characterised in that the ligand L has a structure of the formulae (6) to (10), where the symbols and indices used have the meanings mentioned above:

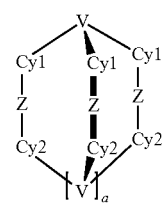

formula (6)

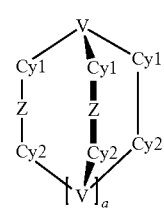

formula (7)

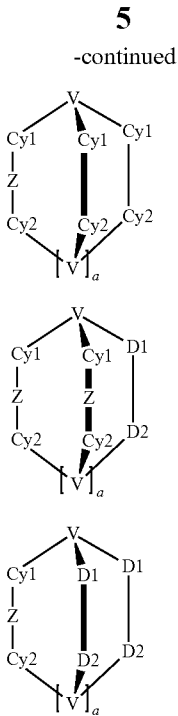

formula (8)

formula (9)

formula (10)

Particular preference is given to compounds of the formula (1) according to the invention, characterised in that L2 and L3 are, identically or differently on each occurrence, L1, i.e. compounds which contain a ligand L of the formula (6).

Preference is furthermore given to metal complexes of the formula (1) where the following applies to the ligand moiety L1 thereof together with the metal and the bridging unit V of the formula (11):

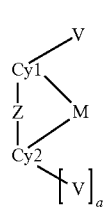

formula (11)

M is a transition metal or aluminium, gallium, indium, tin or lead;
Cy1, Cy2 are, identically or differently on each occurrence, an aryl or heteroaryl group having 5 to 30 aromatic ring atoms, which may be substituted by one or more radicals R, or a cyclic saturated or preferably unsaturated carbene; one of the two groups Cy1 or Cy2 here is bonded to the metal via a formally negatively charged carbon or via a formally negatively charged exocyclic donor atom and the other of the two groups Cy1 and Cy2 is bonded via a neutral donor atom which is part of the group Cy1 or Cy2 and which is selected from nitrogen, phosphorus and carbon in the form of a carbene;
V is, identically or differently on each occurrence, B, BR$^-$, B(CR$_2$)$_3$, RB(CR$_2$)$_3^-$, B(O)$_3$, RB(O)$_3^-$, B(CR$_2$CR$_2$)$_3$, RB(CR$_2$CR$_2$)$_3^-$, B(CR$_2$O)$_3$, RB(CR$_2$O)$_3^-$, B(OCR$_2$)$_3$, RB(OCR$_2$)$_3^-$, Al(O)$_3$, RAl(O)$_3^-$, Al(OCR$_2$)$_3$, RAl(OCR$_2$)$_3^-$, CR, CO$^-$, CN(R$^1$)$_2$, RC(CR$_2$)$_3$, RC(O)$_3$, RC(CR$_2$CR$_2$)$_3$, RC(CR$_2$O)$_3$, RC(OCR$_2$)$_3$, RC(SiR$_2$)$_3$, RC(SiR$_2$CR$_2$)$_3$, RC(CR$_2$SiR$_2$)$_3$, RC(SiR$_2$SiR$_2$)$_3$, SiR, RSi(CR$_2$)$_3$, RSi(O)$_3$, RSi(CR$_2$CR$_2$)$_3$, RSi(OCR$_2$)$_3$, RSi(CR$_2$O)$_3$, RSi(SiR$_2$)$_3$, RSi(SiR$_2$CR$_2$)$_3$, RSi(CR$_2$SiR$_2$)$_3$, RSi(SiR$_2$SiR$_2$)$_3$, N, NO, NR$^+$, N(CR$_2$)$_3$, RN(CR$_2$)$_3^+$, N(C=O)$_3$, N(CR$_2$CR$_2$)$_3$, RN(CR$_2$CR$_2$)$^+$, P, RR$^+$, PO, PS, PSe, PTe, P(O)$_3$, PO(O)$_3$, P(OCR$_2$)$_3$, PO(OCR$_2$)$_3$, P(CR$_2$)$_3$, PR(CR$_2$)$_3^+$, PO(CR$_2$)$_3$, P(CR$_2$CR$_2$)$_3$, PR(CR$_2$CR$_2$)$_3^+$, PO(CR$_2$CR$_2$)$_3$, As, AsR$^+$, AsO, AsS, AsSe, AsTe, As(O)$_3$, AsO(O)$_3$, As(OCR$_2$)$_3$, AsO(OCR$_2$)$_3$, As(CR$_2$)$_3$, AsR(CR$_2$)$_3^+$, AsO(CR$_2$)$_3$, As(CR$_2$CR$_2$)$_3$, AsR(CR$_2$CR$_2$)$_3^+$, AsO(CR$_2$CR$_2$)$_3$, Sb, SbR$^+$, SbO, SbS, SbSe, SbTe, Sb(O)$_3$, SbO(O)$_3$, Sb(OCR$_2$)$_3$, SbO(OCR$_2$)$_3$, Sb(CR$_2$)$_3$, SbR(CR$_2$)$_3^+$, SbO(CR$_2$)$_3$, Sb(CR$_2$CR$_2$)$_3$, SbR(CR$_2$CR$_2$)$_3^+$, SbO(CR$_2$CR$_2$)$_3$, Bi, BiR$^+$, BiO, BiS, BiSe, BiTe, Bi(O)$_3$, BiO(O)$_3$, Bi(OCR$_2$)$_3$, BiO(OCR$_2$)$_3$, Bi(CR$_2$)$_3$, BiR(CR$_2$)$_3^+$, BiO(CR$_2$)$_3$, Bi(CR$_2$CR$_2$)$_3$, BiR(CR$_2$CR$_2$)$_3^+$, BiO(CR$_2$CR$_2$)$_3$, S$^+$, S(CR$_2$)$_3^+$, S(CR$_2$CR$_2$)$_3^+$, Se$^+$, Se(CR$_2$)$_3^+$, Se(CR$_2$CR$_2$)$_3^+$, Te$^+$, Te(CR$_2$)$_3^+$, Te(CR$_2$CR$_2$)$_3^+$, cyclopropane, which is linked via the 1-, 2- and 3-position, aziridine, which is linked via the 1-, 2- and 3-positions, or corresponding asymmetrical analogues; or a unit of the formula (12), (13) or (14)

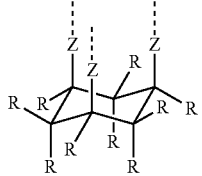

formula (12)

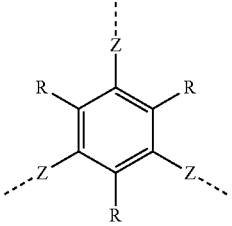

formula (13)

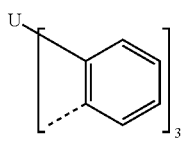

formula (14)

where U stands for N, P, P(=O), CR or SiR, and the dashed bonds each indicate the bond to the ligand moieties;
Z is, identically or differently on each occurrence, O, S, S(=O), S(=O)$_2$, NR, PR, P(=O)R, P(=NR), CR$_2$, C(=O), C(=NR), C(=CR$_2$), SiR$_2$ or BR;
R is on each occurrence, identically or differently, H, D, F, Cl, Br, I, N(R$^1$)$_2$, CN, NO$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals R$^1$, where one or more non-adjacent CH$_2$ groups may be replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, O, S or CONR$^1$ and where one or more H atoms may be replaced by F, Cl, Br, I, CN or NO$_2$, or an aromatic or hetero-aromatic ring system having 5 to 60 aromatic ring atoms, which may in each case be substituted by one or more radicals R¹, or an aryloxy or heteroaryloxy group having 5 to 60 aromatic ring atoms, which may be substituted by one or more radicals R¹, or a diarylamino group, diheteroarylamino group or arylheteroaryl-amino group having 10 to 40 aromatic ring atoms, which may be substituted by one or more radicals R¹, or a combination of these systems; two or more substituents R here may also form a mono- or polycyclic aliphatic, aromatic and/or benzo-fused ring system with one another;

R¹ is on each occurrence, identically or differently, H, F or an aliphatic, aromatic and/or heteroaromatic hydrocarbon radical having 1 to 20 C atoms, in which, in addition, one or more H atoms may be replaced by F; two or more substituents R¹ here may also form a mono- or polycyclic aliphatic or aromatic ring system with one another;

a is as defined above.

The preferred structure of the formula (11) shown above is also preferred for the moieties comprising the ligand moiety L2 or L3 together with the metal and the bridging unit V in the case where L2 or L3 stands for a group of the formula (3).

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc. For the purposes of this invention, a cyclic carbene is a cyclic group which is bonded to the metal via a neutral C atom. The cyclic group here may be saturated or unsaturated. Preference is given here to Arduengo carbenes, i.e. carbenes in which two nitrogen atoms are bonded to the carbene C atom.

For the purposes of this invention, an aromatic ring system contains 6 to 60 C atoms in the ring system. For the purposes of this invention, a hetero-aromatic ring system contains 2 to 60 C atoms and at least one hetero-atom in the ring system, with the proviso that the sum of C atoms and heteroatoms is at least 5. The heteroatoms are preferably selected from N, O and/or S. For the purposes of this invention, an aromatic or hetero-aromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an sp³-hybridised C, N or O atom. Thus, for example, systems such as 9,9'-spirobifluorene, 9,9-diarylfluorene, triaryl-amine, diary' ether, stilbene, etc., are also intended to be taken to mean aromatic ring systems for the purposes of this invention, and likewise systems in which two or more aryl groups are interrupted, for example, by a linear or cyclic alkyl group or by a silyl group.

For the purposes of the present invention, a $C_1$- to $C_{40}$-alkyl group, in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methyl-butyl, n-pentyl, s-pentyl, cyclopentyl, n-hexyl, cyclohexyl, n-heptyl, cyclo-heptyl, n-octyl, cyclooctyl, 2-ethylhexyl, trifluoromethyl, pentafluoroethyl and 2,2,2-trifluoroethyl. An alkenyl group is preferably taken to mean the radicals ethenyl, propenyl, butenyl, pentenyl, cyclopentenyl, hexenyl, cyclohexenyl, heptenyl, cycloheptenyl, octenyl and cyclooctenyl. An alkynyl group is preferably taken to mean ethynyl, propynyl, butynyl, pentynyl, hexynyl, heptynyl and octynyl. A $C_1$- to $C_{40}$-alkoxy group is preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic group via any desired positions, is taken to mean, in particular, groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Particularly preferred moieties of the formula (11) mentioned above are the moieties of the formulae (15) to (30):

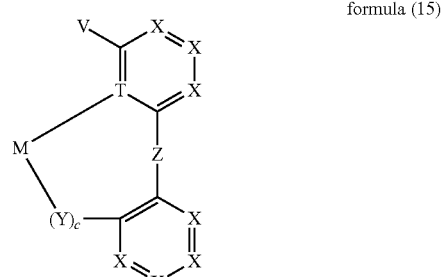

formula (15)

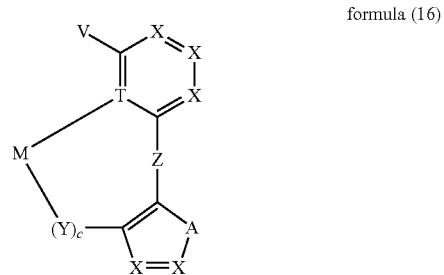

formula (16)

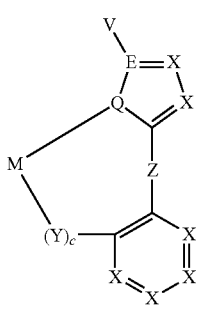
formula (17)
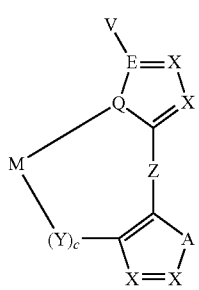
formula (18)
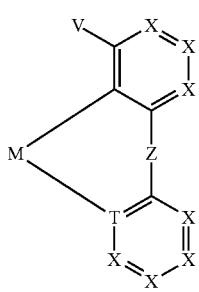
formula (19)
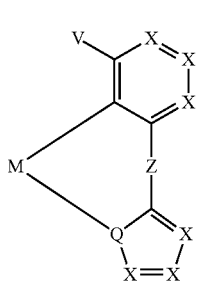
formula (20)
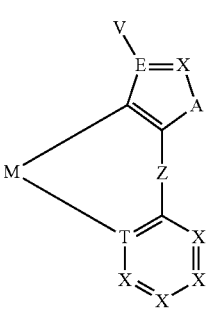
formula (21)
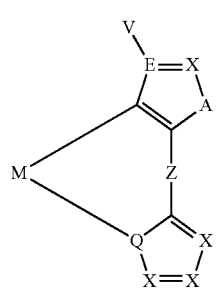
formula (22)
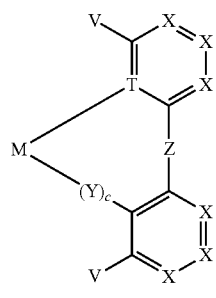
formula (23)
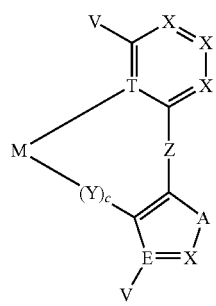
(formula 24)
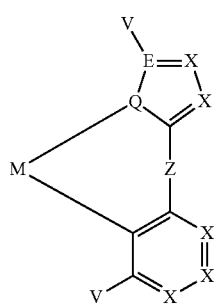
formula (25)
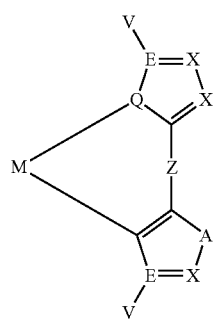
formula (26)

-continued formula (27)

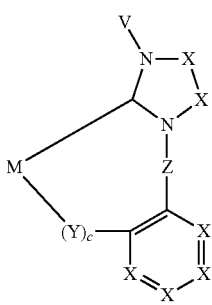

formula (28)

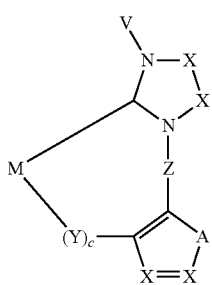

formula (29)

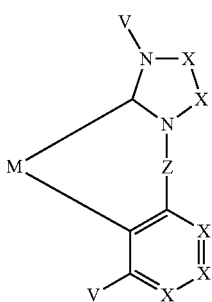

formula (30)

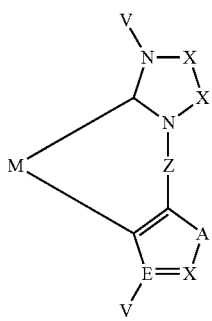

where M, Z, V, R and $R^1$ have the meanings mentioned above under formula (10) and furthermore:

E is, identically or differently on each occurrence, C, N or P;

Q is, identically or differently on each occurrence, O, S, Se, Te or N;

T is, identically or differently on each occurrence, N, P or C;

A is, identically or differently on each occurrence, $NR^1$, S or O

X is, identically or differently on each occurrence, CR, N or P, where in this case a double bond is present between the two groups X in the carbene ring in the formulae (27), (28), (29) and (30); or X in the carbene ring in the formulae (27), (28), (29) and (30) stands, identically or differently on each occurrence, for $CR_2$;

Y is, identically or differently on each occurrence, $NR^1$, $COO^-$, O, S, Se, Te, SO, SeO, TeO, $SO_2$, $SeO_2$, $TeO_2$, $R^1SO$, $R^1SeO$, $R^1TeO$, $R^1SO_2$, $R^1SeO_2$, $R^1TeO_2$, $R^1PO$ or $(R^1)_2PO$;

c is, identically or differently on each occurrence, 0 or 1.

The moieties of the formulae (15) to (30), considered without the metal M and without the bridging unit(s) V, correspond here to the ligand moiety L1.

Preference is given to compounds of the formula (1) and of the formulae (6) to (10) and compounds containing a moiety of the formula (11) or of the formulae (15) to (30) in which M stands for a hexacoordinated transition-metal ion having an atomic number greater than 38, particularly preferably for tungsten, rhenium, ruthenium, osmium, rhodium, iridium, platinum or gold, in particular iridium. The metals here can be in various oxidation states. Preference is given here to the above-mentioned metals in the oxidation states W(II), W(III), W(IV), Re(II), Re(III), Re(IV), Ru(II), Ru(III), Os(II), Os(III), Rh(III), Ir(III), Ir(IV), Pt(IV) and Au(III); particular preference is given to iridium(III) and platinum(IV). Preference is furthermore given to compounds of the formula (1) in which M stands for Sc(III), Y(III), La(III), Al(III), Ga(III) or In(III), in particular for Al(III).

Preference is furthermore given to compounds containing a moiety of the formulae (15) to (30) in which Q on each occurrence, identically or differently, stands for O, S or N, particularly preferably for O or S.

Preference is furthermore given to compounds containing a moiety of the formulae (15) to (30) in which E on each occurrence, identically or differently, stands for C or N, particularly preferably for C.

Preference is furthermore given to compounds containing a moiety of the formulae (15) to (30) in which T on each occurrence, identically or differently, stands for N or P, particularly preferably for N.

Preference is furthermore given to compounds containing a moiety of the formulae (15) to (30) in which X on each occurrence, identically or differently, stands for CR or N.

Preference is furthermore given to compounds containing a moiety of the formulae (15) to (30) in which Y on each occurrence, identically or differently, stands for O, S or $NR^1$, particularly preferably for O.

Preference is furthermore given to compounds of the formula (1) and of the formulae (6) to (10) and compounds containing a moiety of the formula (11) or of the formulae (15) to (30) in which Z on each occurrence, identically or differently, stands for O, S, NR, $CR_2$, C(=O) or C(=$CR_2$).

Preference is furthermore given to compounds of the formula (1) and of the formulae (6) to (10) and compounds containing a moiety of the formula (11) or of the formulae (15) to (30) in which V stands for B, $BR^-$, CR, $CO^-$, $CN(R^1)_2$, SiR, N, NO, $NR^+$, P, $PR^+$, PO, PS, As, AsO, AsS, Sb, SbO, SbS, $S^+$ or $Se^+$, in particular for CR, $CO^-$, N, $NR^+$, P, $PR^+$ or PO.

Preference is furthermore given to compounds of the formula (1) and of the formulae (6) to (10) and compounds containing a moiety of the formula (11) or of the formulae (15) to (30), in which the index c=0.

Particular preference is given to compounds of the formula (1) and of the formulae (6) to (10) and compounds containing a moiety of the formula (11) or of the formulae (15) to (30) in which the preferences mentioned above apply simultaneously.

Preference is furthermore given to compounds of the formula (1) and of the formulae (6) to (10) and compounds containing a moiety of the formula (11) or of the formulae (15) to (30) in which R stands on each occurrence, identically or differently, for F, CN, a straight-chain alkyl or alkoxy group having 1 to 6 C atoms or a branched or cyclic alkyl or alkoxy group having 3 to 6 C atoms, each of which may be substituted by one or more radicals $R^1$, where one or more non-adjacent $CH_2$ groups may be replaced by $R^1C=CR^1$, O or S and one or more H atoms may be replaced by F, or an aryl or heteroaryl group having 5 to 16 aromatic ring atoms, which may in each case be substituted by one or more radicals $R^1$, or a diarylamino group having 10 to 20 aromatic ring atoms, which may be substituted by one or more radicals $R^1$, or a combination of these systems; two or more substituents R here may also form a mono- or polycyclic aliphatic, aromatic and/or benzo-fused ring system with one another. The symbol R particularly preferably stands, identically or differently on each occurrence, for F, a straight-chain alkyl group having 1 to 4 C atoms or a branched alkyl group having 3 or 4 C atoms, each of which may be substituted by one or more radicals $R^1$, where one or more H atoms may be replaced by F, or an aryl group having 6 to 10 aromatic ring atoms, which may be substituted by one or more radicals $R^1$; two or more substituents R here may also form a mono- or polycyclic aliphatic, aromatic and/or benzo-fused ring system with one another.

Preference is furthermore given to symmetrical compounds, in particular compounds in which the ligand moieties L1 and L2 are identical and are also identically substituted or in which all three ligand moieties L1, L2 and L3 are identical and are also identically substituted.

If the ligand moiety L2 and/or L3 has a structure of the formula (4), these are preferably structures of the following formulae (31) to (47):

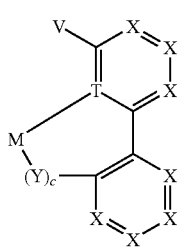

formula (31)

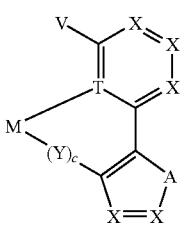

formula (32)

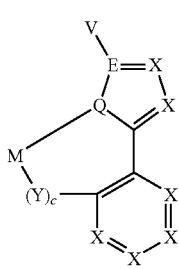

formula (33)

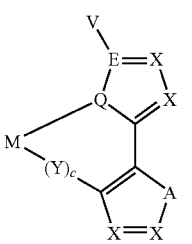

formula (34)

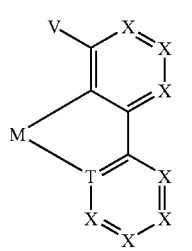

formula (35)

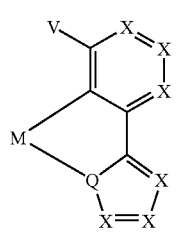

formula (36)

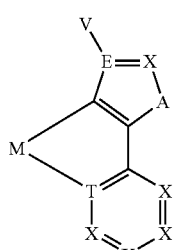

formula (37)

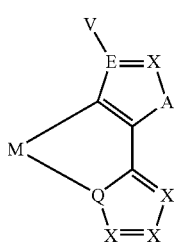

formula (38)

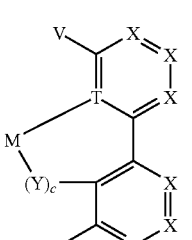

formula (39)

formula (40)

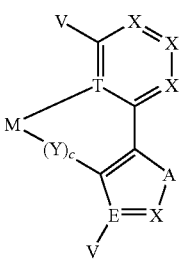

formula (41)

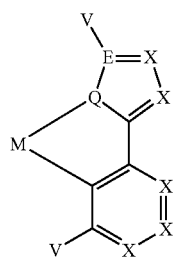

formula (42)

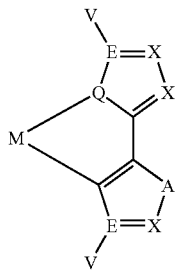

formula (43)

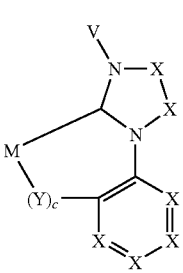

formula (44)

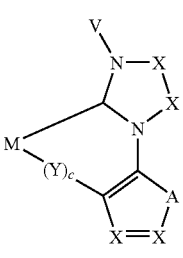

formula (45)

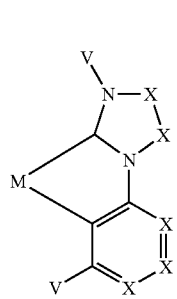

formula (46)

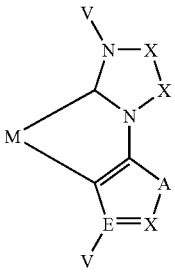

X here is, identically or differently on each occurrence, CR, N or P, where in this case a double bond is present between the two groups X in the carbene ring in the formulae (43), (44), (45) and (46); or X in the carbene ring in the formulae (43), (44), (45) and (46) stands, identically or differently on each occurrence, for $CR_2$. The other symbols and indices have the same meaning as given above for the structures of the formulae (15) to (30). Furthermore, the preferred embodiments given above apply to the individual symbols.

If the ligand moiety L2 and/or L3 has a structure of the formula (5), a bidentate chelating ligand containing two groups D1 and D2 is involved, where the corresponding donor atoms are preferably selected from the fifth and sixth main group or represent isonitrile groups. Furthermore, the complexed ligand moiety L2 or L3 preferably does not have a direct metal-carbon bond. A wide variety of suitable bidentate ligands are known to the person skilled in the art, and many examples are given in Cotton, Wilkinson, *Anorganische Chemie* [Inorganic Chemistry], 2nd Edition, Verlag Chemie, Weinheim, 1970, pp. 917-972.

Particularly preferred donor atoms in groups D1 and D2 are nitrogen, phosphorus, oxygen and sulfur, in particular nitrogen and oxygen.

Preferred nitrogen-containing donor groups are aromatic nitrogen hetero-cycles, for example pyridine, quinoline, isoquinoline, pyrazine, quinoxaline, pyrimidine, pyridazine, triazine, pyrrole, indole, imidazole, benzimidazole, pyrazole or triazole, aliphatic amines, aliphatic cyclic amines, for example pyrrolidine, piperidine or morpholine, nitriles, amides, imides and imines, each of which may be substituted by groups R or unsubstituted.

Preferred phosphorus-containing donor groups are alkyl-, aryl- or mixed alkylarylphosphines, alkylhalo-, arylhalo- or mixed alkylarylhalophosphines, alkyl, aryl or mixed alkyl aryl phosphites or phospha-aromatic compounds, such as, for example, phosphabenzene, each of which may be substituted by groups R or unsubstituted.

Preferred oxygen-containing donor groups are alcohols, alkoxides, open-chain or cyclic ethers, carbonyl groups, phosphine oxide groups, sulfoxide groups, carboxylates, phenols, phenolates, oximes, hydroxamates, β-ketoketonates, β-ketoesters and β-diesters, each of which may be substituted by groups R or unsubstituted, where the last-mentioned groups are bidentate chelating ligands.

Preferred sulfur-containing donor groups are aliphatic or aromatic thiols and thiolates, open-chain or cyclic thioethers, thiophene, thiocarbonyl groups, phosphine sulfides and thiocarboxylates, each of which may be substituted by groups R or unsubstituted.

The preferred bidentate chelating ligand moieties L2 and L3 of the formula (5) can be formed from these donor groups by combining two of these groups, which may be identical or different and may have identical or different donor atoms. The ligand moieties L2 and L3 formed in this way are covalently bonded to the linking unit V and may also be substituted by one or more radicals R.

Examples of ligand moieties L2 and L3 of the formula (5) of this type are substituted or unsubstituted β-ketoketonates, β-ketoesters, β-diesters, carboxylates derived from aminocarboxylic acids, such as, for example, pyridine-2-carboxylic acid, quinoline-2-carboxylic acid, glycine, dimethylglycine, alanine or dimethylaminoalanine, iminoacetoacetonates, hydroxamates, pyridylphosphines, α-phosphinocarboxylates, glycol ethers, ether alcoholates, dialcoholates derived from dialcohols, such as, for example, ethylene glycol or 1,3-propylene glycol, dithiolates derived from dithiols, such as, for example, 1,2-ethylenedithiol or 1,3-propylenedithiol, diamines, such as, for example, ethylenediamine, propylenediamine or cis- or trans-diaminocyclohexane, imines, such as, for example, 2-[(1-(phenylimino)-ethyl]pyridine, 2-[(1-(2-methylphenylimino)ethyl]pyridine, 2-[(1-(2,6-diisopropylphenylimino)ethyl]pyridine, 2-[(1-(methylimino)ethyl]pyridine, 2-[(1-(ethylimino)ethyl]pyridine, 2-[(1-(isopropylimino)ethyl]pyridine or 2-[(1-(tert-butylimino)ethyl]pyridine, diimines, such as, for example, 1,2-bis(methyl-imino)ethane, 1,2-bis(ethylimino)ethane, 1,2-bis(isopropylimino)ethane, 1,2-bis(tert-butylimino)ethane, 2,3-bis(methylimino)butane, 2,3-bis(ethyl-imino)butane, 2,3-bis(isopropylimino)butane, 2,3-bis(tert-butylimino)-butane, 1,2-bis(phenylimino)ethane, 1,2-bis(2-methylphenylimino)ethane, 1,2-bis(2,6-diisopropylphenylimino)ethane, 1,2-bis(2,6-di-tert-butylphenyl-imino)ethane, 2,3-bis(phenylimino)butane, 2,3-bis(2-methylphenylimino)-butane, 2,3-bis(2,6-diisopropylphenylimino)butane or 2,3-bis(2,6-di-tert-butylphenylimino)butane, diphosphines, such as, for example, bis-diphenylphosphinomethane, bisdiphenylphosphinoethane, bis(diphenylphosphino)propane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane or bis(tert-butylphosphino)propane, salicyliminates derived from salicylimines, such as, for example, methylsalicylimine, ethylsalicylimine or phenylsalicylimine, substituted or unsubstituted hydroxyquinolinates, etc. However, it is straightforward for the person skilled in the art, without further inventive step, to form further ligand moieties L2 or L3 of the formula (5) from the donor groups D1 and D2 mentioned and to employ them in the ligands L and the corresponding metal complexes of the formula (1).

The corresponding ligands L of the formula (2), which represent valuable intermediates for the synthesis of the complexes according to the invention, are novel and are therefore likewise a subject-matter of the present invention. The preferences described above for complexes of the formula (1) also apply here to the corresponding ligands of the formula (2).

The complexes of the formula (1) according to the invention can in principle be prepared by various processes, where, however, the processes described below have proven particularly suitable.

The present invention therefore furthermore relates to a process for the preparation of the complexes of the formula (1) by reaction of the ligands of the formula (2) or precursors of these ligands with metal alkoxides of the formula (47), with metal ketoketonates of the formula (48) or with metal halides of the formula (49):

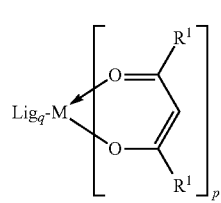

formula (47)
formula (48)
formula (49)

where M and $R^1$ have the same meaning as described above, and the following applies to the other symbols and indices:

Hal is on each occurrence, identically or differently, F, Cl, Br or I;

Lig is on each occurrence, identically or differently, a neutral or monoanionic, monodentate or bidentate ligand, for example a halide or hydroxide;

p is on each occurrence, identically or differently, 1, 2, 3, 4 or 5, where p in formulae (47) and (49) indicates the valency of the metal M;

q is on each occurrence, identically or differently, 0, 1, 2, 3 or 4, preferably 0, 1 or 2;

the compound of the formula (48) here may also be charged and may also contain a counterion.

Particularly preferred starting compounds are compounds of the formula (48), in particular the compound $Na[IrCl_2(acac)_2]$ or $IrCl_3$ hydrate.

The synthesis can, for example, be activated thermally, photochemically or by microwave radiation. The synthesis of tris-ortho-metallated metal complexes is described in general in WO 02/060910, WO 04/085449 and WO 04/108738, WO 07/065,523. The synthetic methods and preferred reaction conditions disclosed in these specifications can be applied analogously to the synthesis of compounds of the formula (1).

In a preferred synthetic method, the ligand L of the formula (2) is reacted with metal compounds, as described by formulae (47), (48) and (49). This synthetic method is shown in Scheme 1:

Scheme 1:

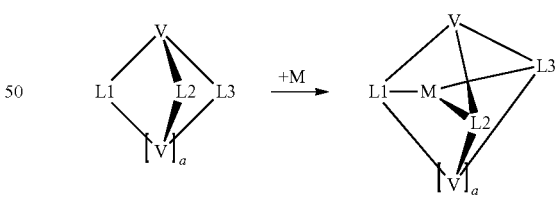

A further preferred synthetic method for the complexes and cryptates according to the invention has proven to be template synthesis, as shown in Scheme 2. To this end, metal compounds, as described by the formulae (47), (48) and (49), are reacted with a simple, macrocyclic or polypodal precursor of the ligand, where the ligand precursor is derived from the ligand through having no or only one bridging unit V instead of one or two or through containing only two of the three ligand moieties L1, L2 and L3. In a second synthetic step, the bridging unit V is then introduced in a complex-analogous reaction, i.e. a reaction on the metal complex, or both bridging units V are introduced, or the third ligand moiety L1 or L2 or L3 is introduced and linked to the bridging units V. These synthetic methods have the advantage that the complex formation that has already taken place means that the three ligand moieties L1, L2 and L3 are present in a spatially preferred arrangement, which facilitates simple ring closure for the introduction of V or for the linking of the third ligand moiety, which is only possible with greater technical complexity on use of the uncomplexed ligand moieties. These synthetic methods are shown in Scheme 2:

Scheme 2:
Synthesis with formation of a bridging unit V:

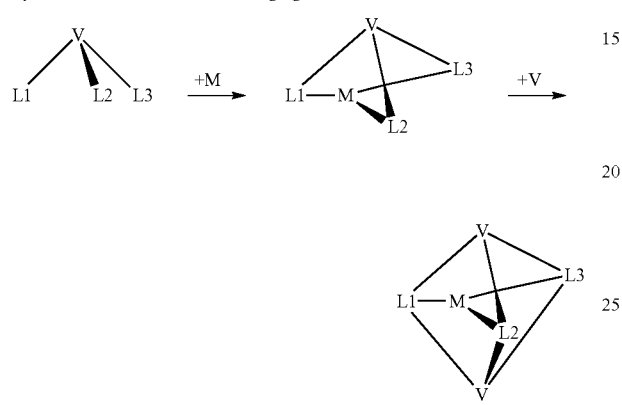

Synthesis with formation of all bridging units V:

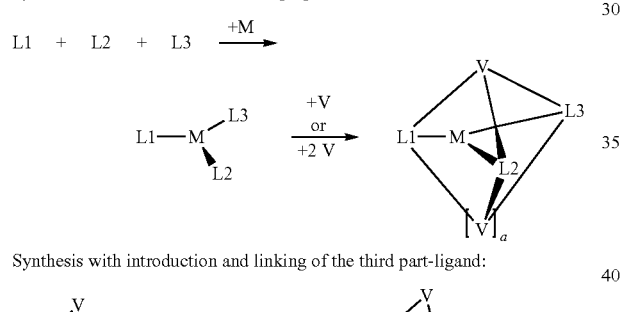

Synthesis with introduction and linking of the third part-ligand:

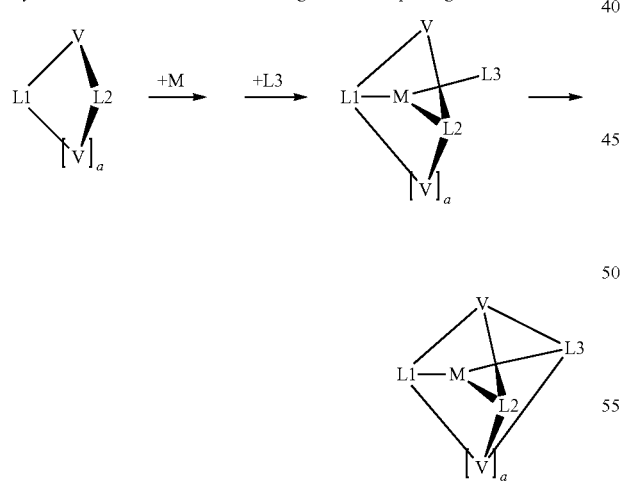

These methods give the complexes easily in high purity, preferably in a purity of >99% according to $^1$H-NMR or HPLC.

Examples of preferred compounds of the formula (1) are compounds (1) to (264) depicted below. These complexes can be prepared, inter alia, using the synthetic methods explained above.

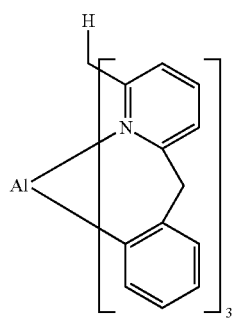

(1)

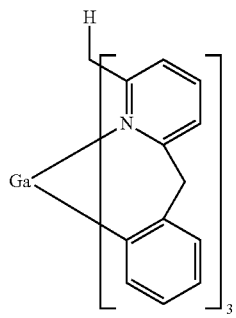

(2)

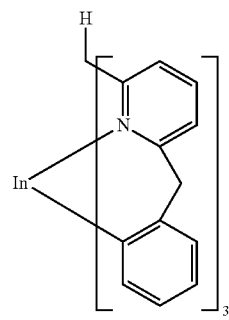

(3)

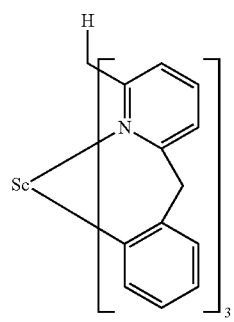

(4)

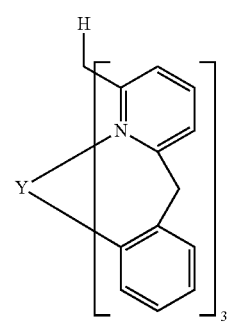

(5)

-continued (6) [structure with La] ₃

(7) [structure with Ti] ₃

(8) [structure with Zr] ₃

(9) [structure with Hf] ₃

(10) [structure with V] ₃

(11) [structure with Nb] ₃

(12) [structure with Ta] ₃

(13) [structure with Cr] ₃

(14) [structure with Mo] ₃

(15) [structure with W] ₃

(16)
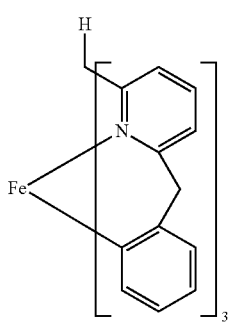
(17)
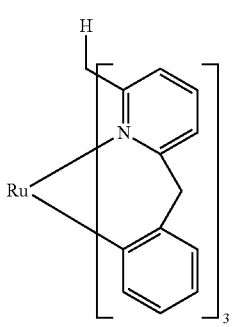
(18)
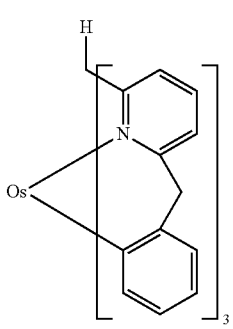
(19)
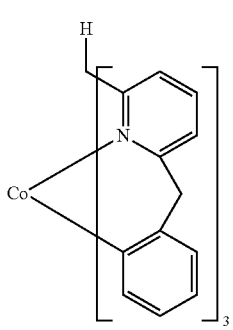
(20)
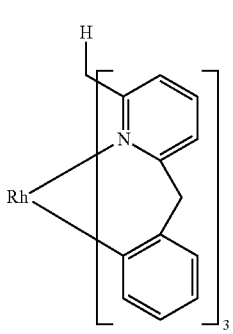
(21)
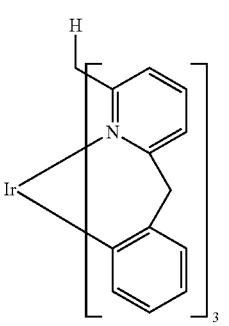
(22)
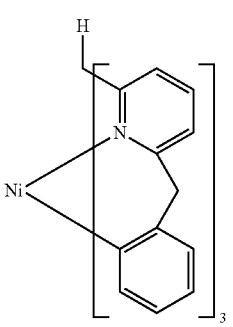
(23)
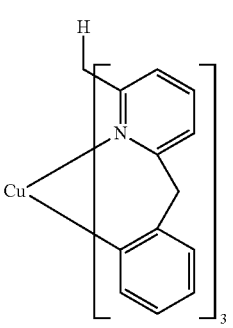
(24)
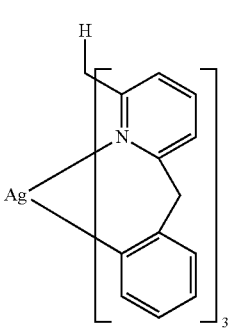
(25)
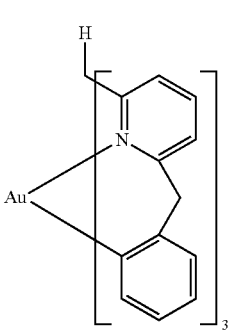

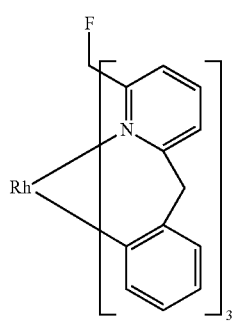 (26)
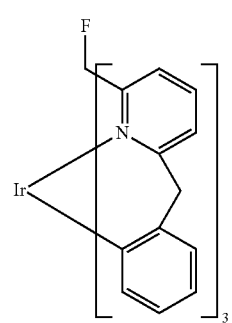 (27)
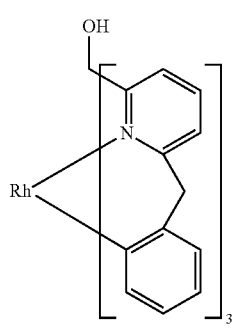 (28)
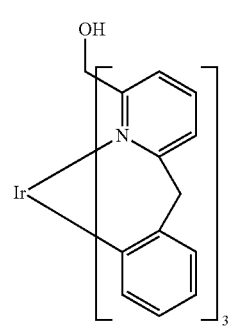 (29)
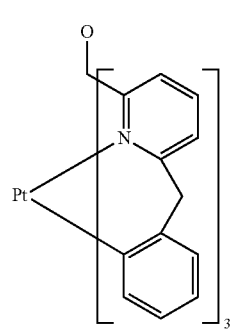 (30)
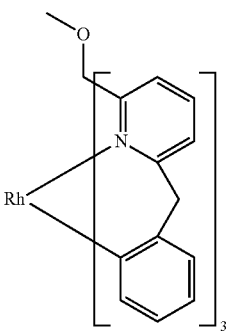 (31)
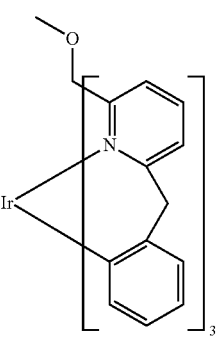 (32)
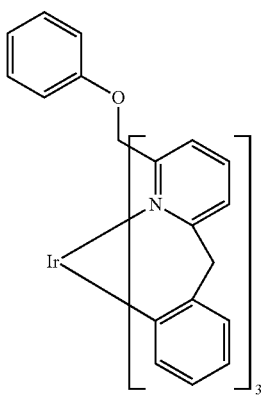 (33)
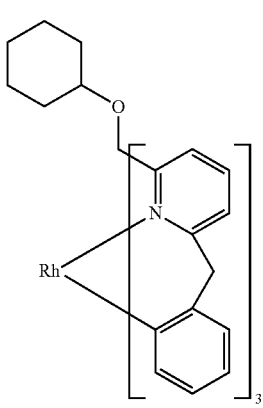 (34)

(35) 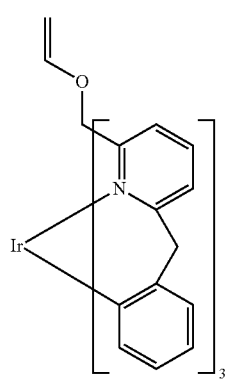
(36) 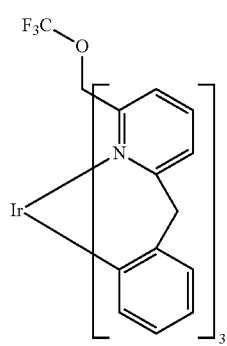
(37) 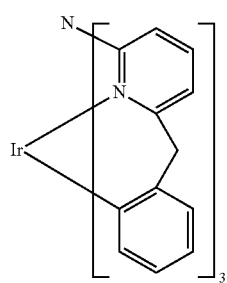
(38) 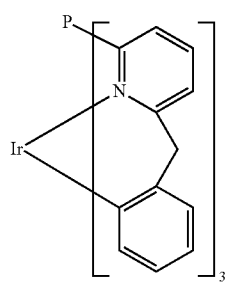
(39) 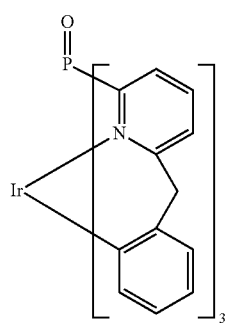
(40) 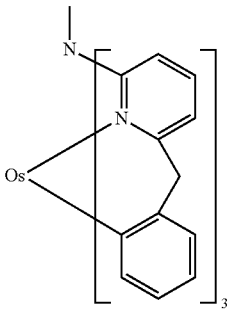
(41) 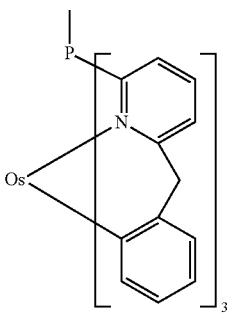
(42) 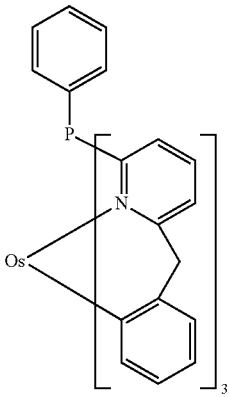
(43) 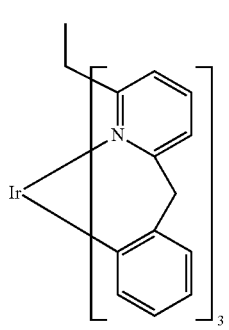

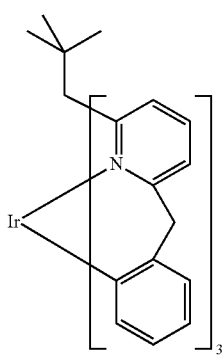
(44)
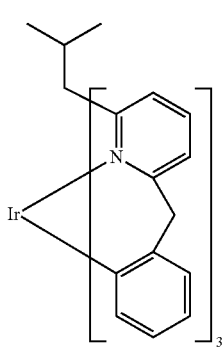
(45)
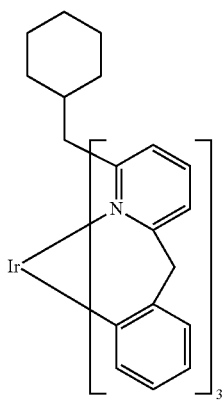
(46)
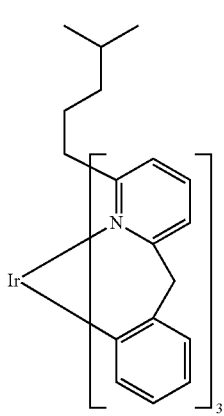
(47)
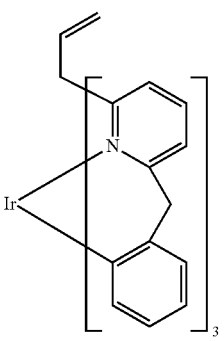
(48)
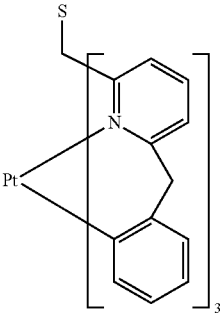
(49)
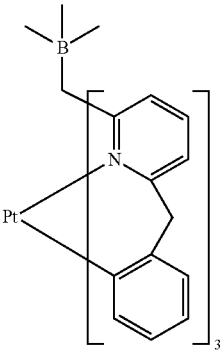
(50)
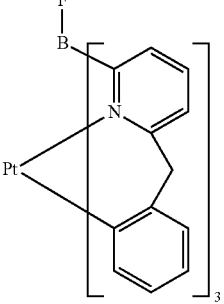
(51)
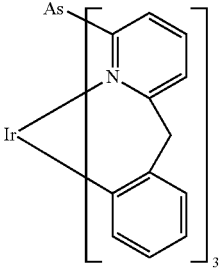
(52)

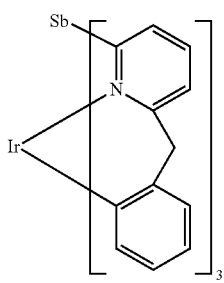 (53)
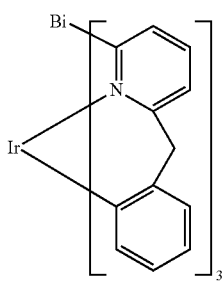 (54)
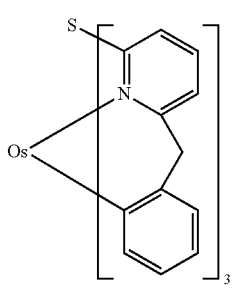 (55)
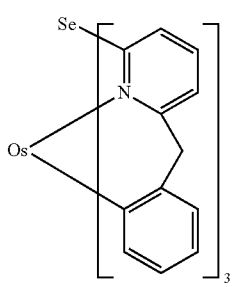 (56)
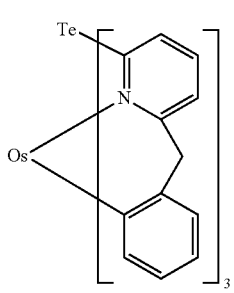 (57)
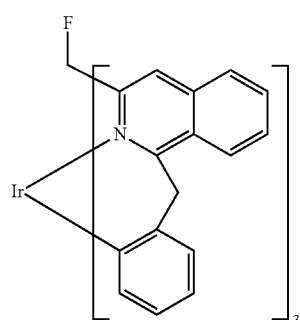 (58)
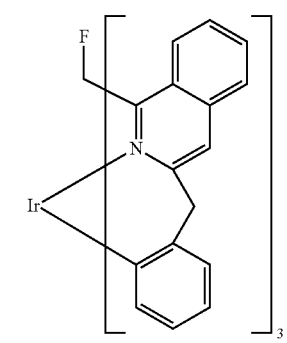 (59)
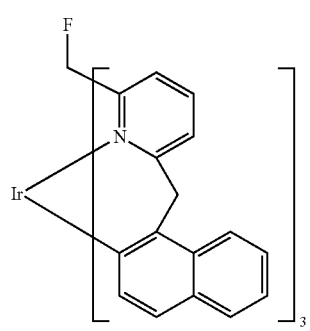 (60)
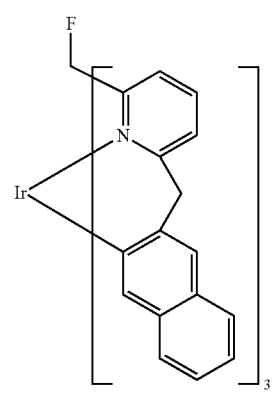 (61)

-continued
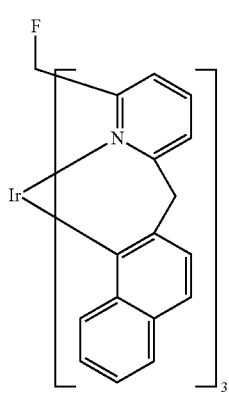
(62)
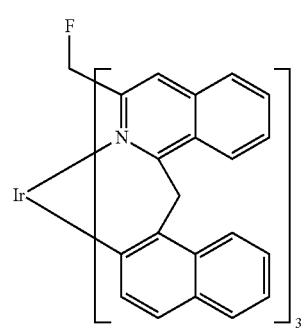
(63)
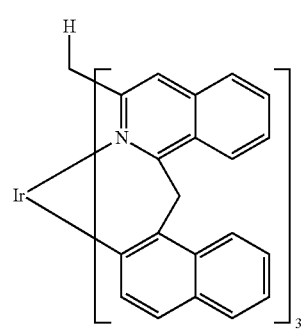
(64)
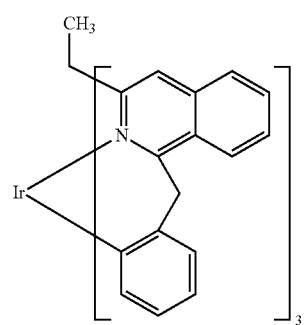
(65)
-continued
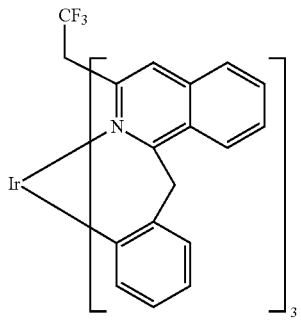
(66)
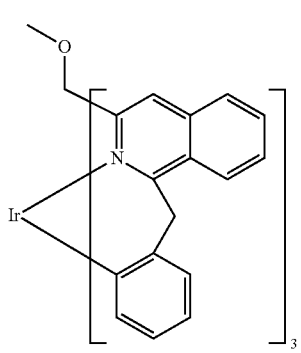
(67)
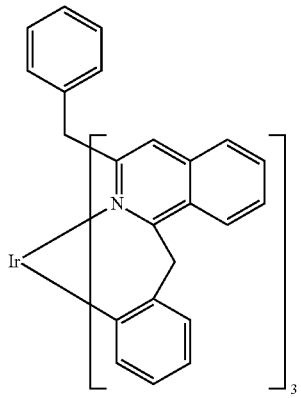
(68)
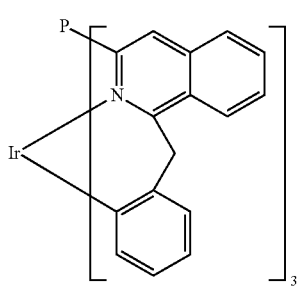
(69)

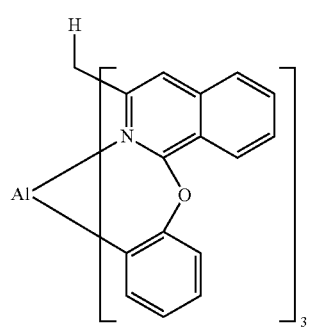
(70)
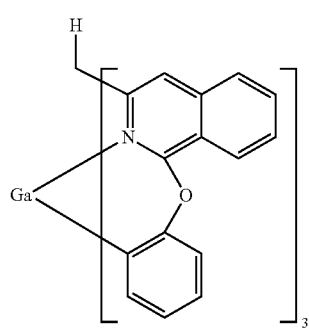
(71)
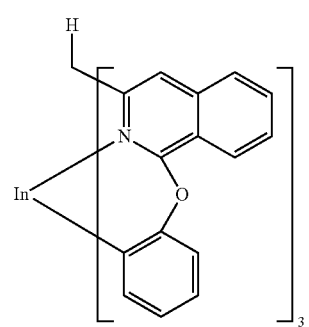
(72)
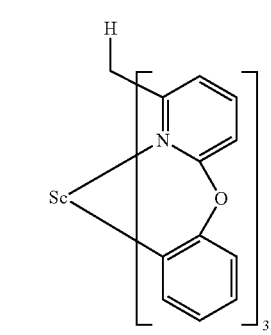
(73)
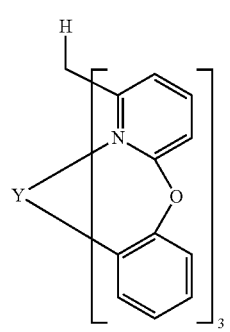
(74)
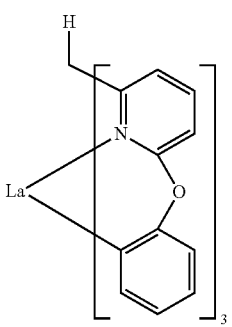
(75)
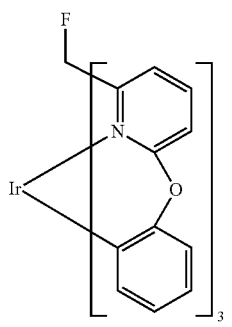
(76)
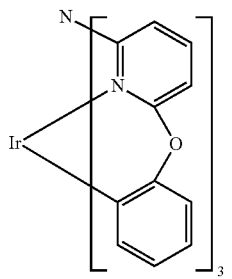
(77)
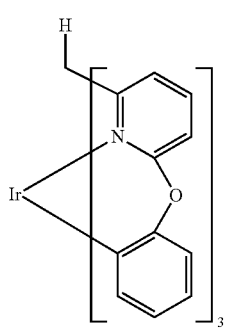
(78)
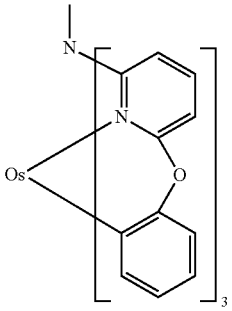
(79)

(80)
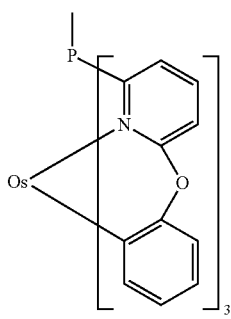
(81)
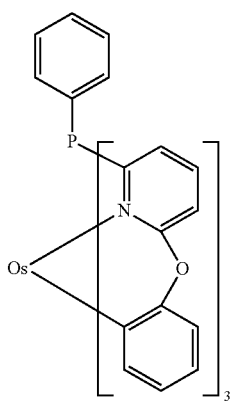
(82)
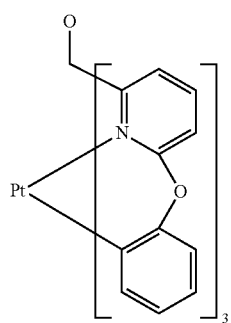
(83)
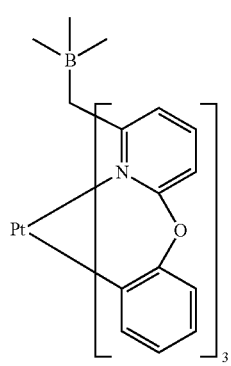
(84)
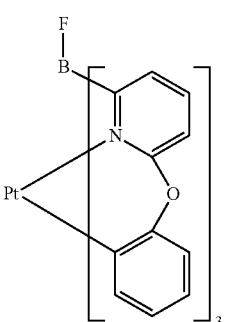
(85)
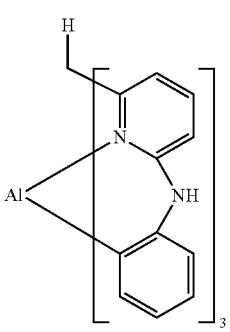
(86)
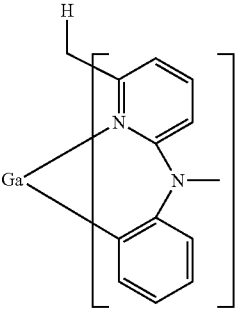
(87)
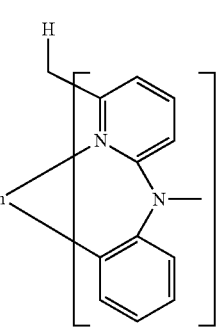
(88)
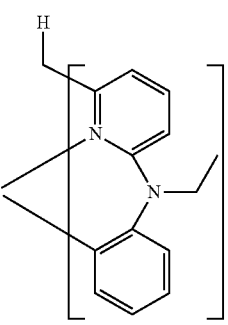

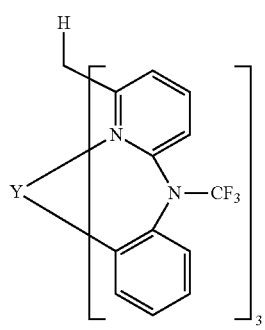 (89)
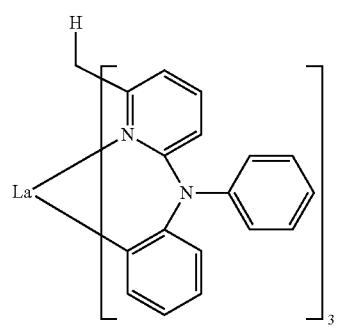 (90)
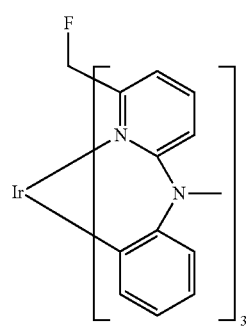 (91)
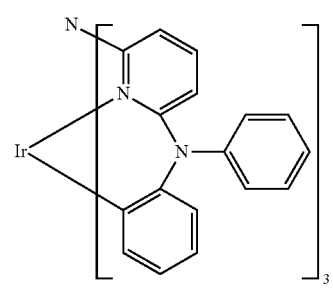 (92)
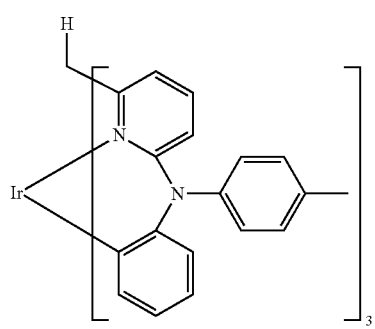 (93)
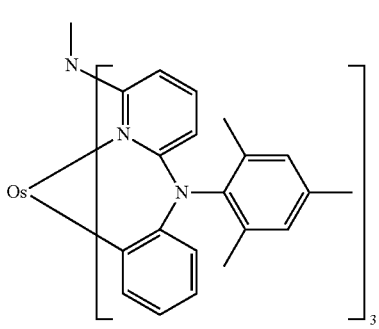 (94)
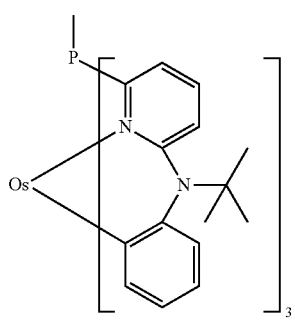 (95)
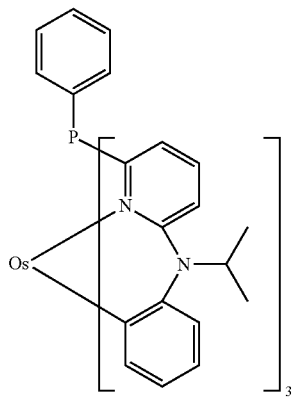 (96)
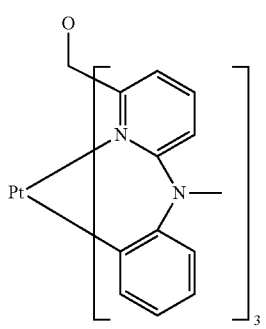 (97)

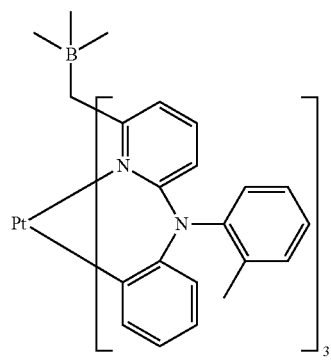
(98)
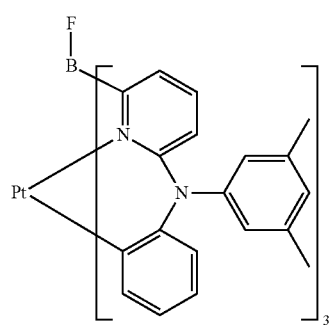
(99)
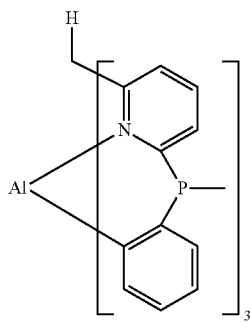
(100)
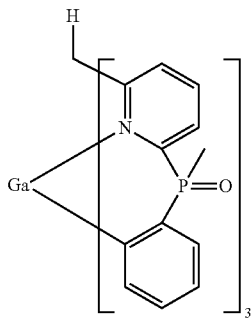
(101)
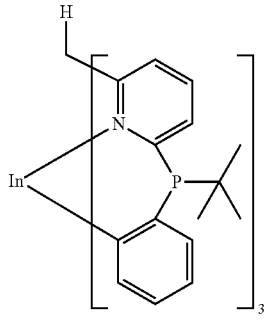
(102)
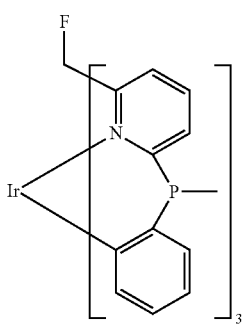
(103)
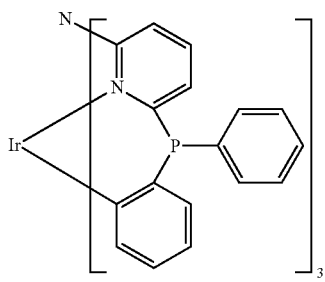
(104)
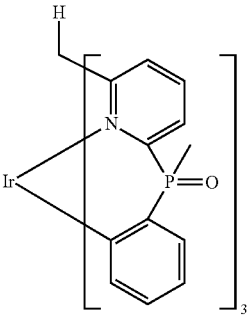
(105)
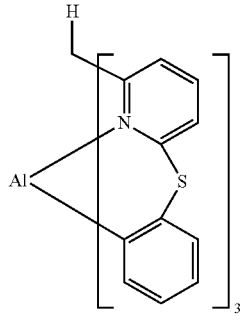
(106)
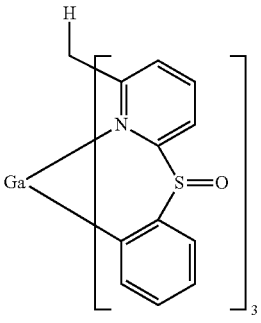
(107)

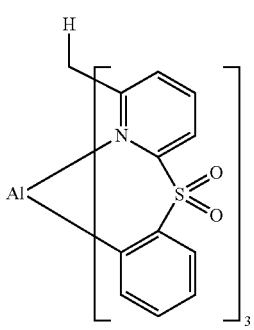 (108)
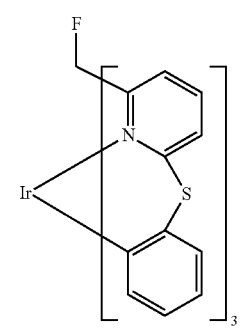 (109)
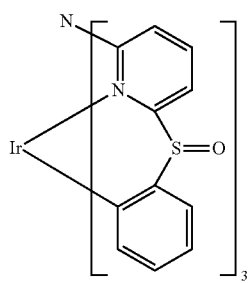 (110)
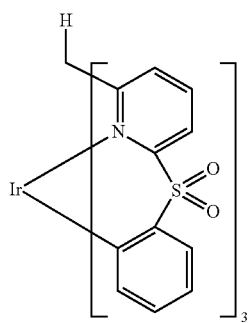 (111)
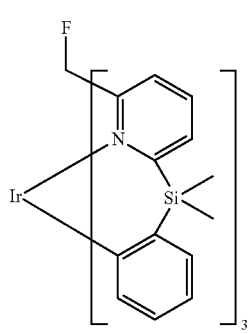 (112)
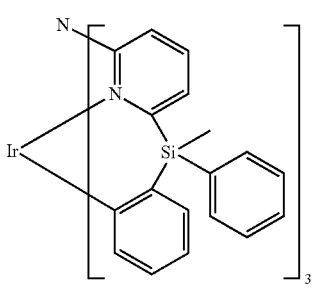 (113)
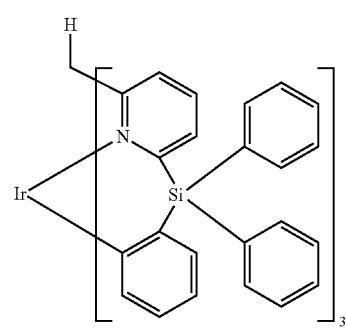 (114)
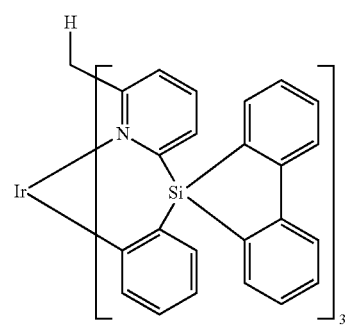 (115)
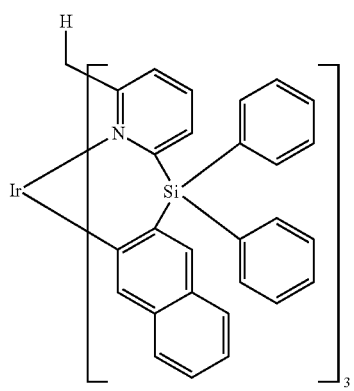 (116)

(117)
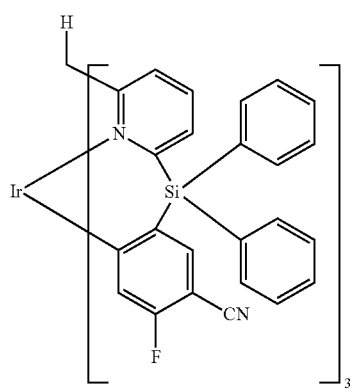
(118)
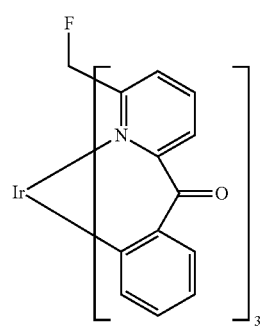
(119)
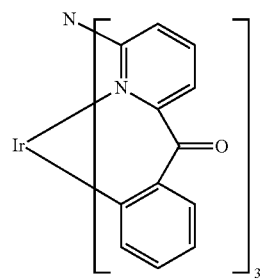
(120)
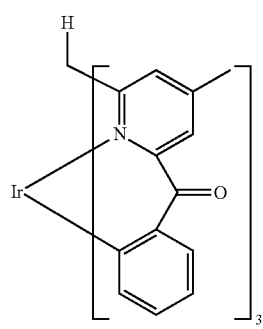
(121)
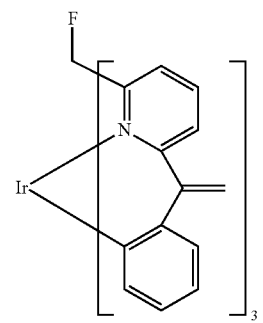
(122)
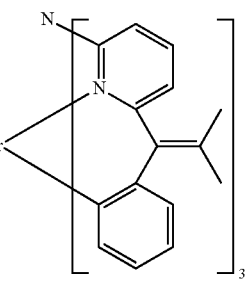
(123)
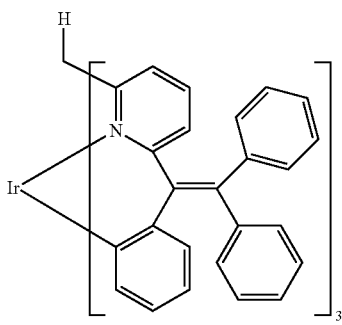
(124)
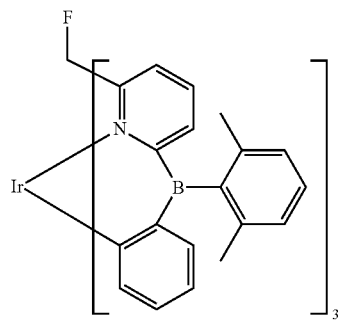
(125)
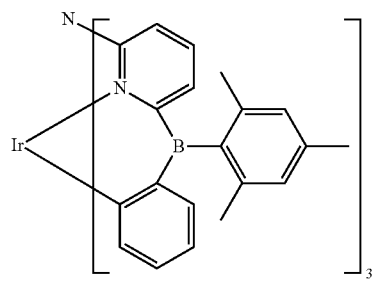
(126)
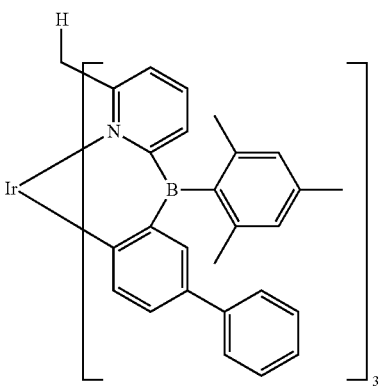

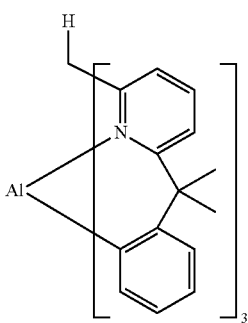 (127)
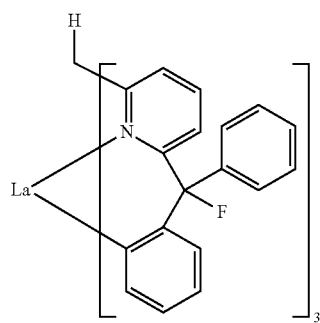 (132)
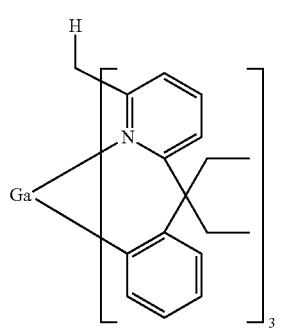 (128)
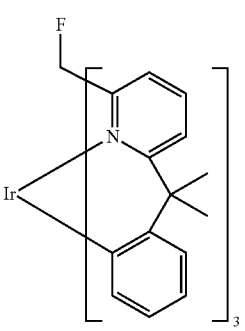 (133)
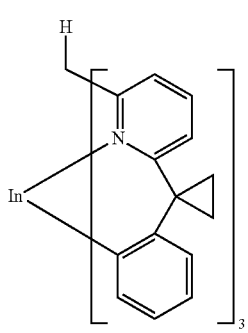 (129)
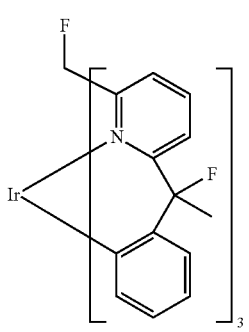 (134)
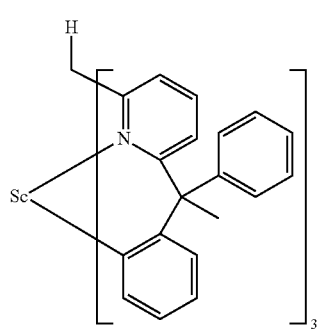 (130)
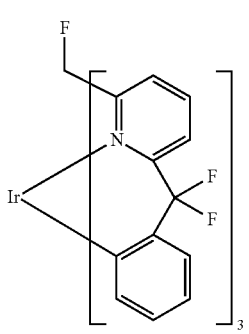 (135)
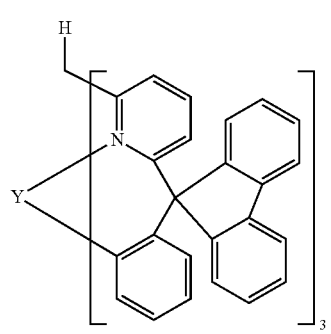 (131)
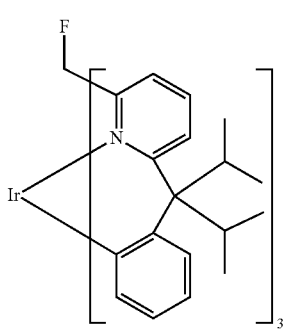 (136)

-continued
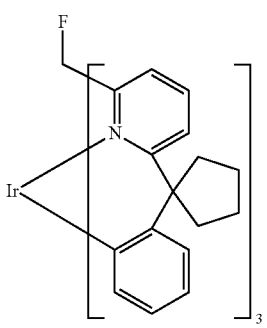 (137)
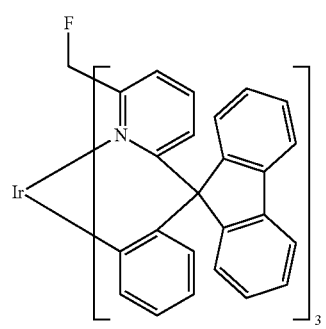 (138)
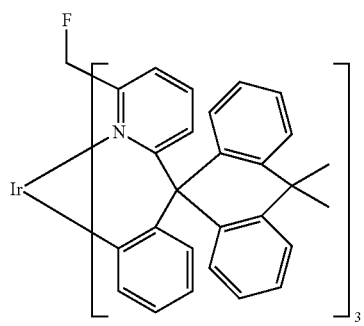 (139)
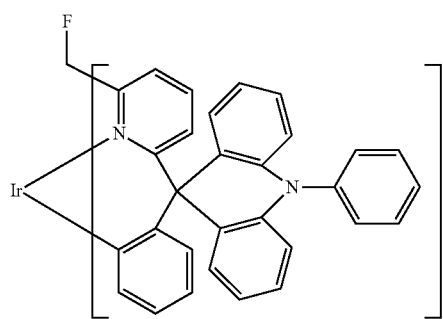 (140)
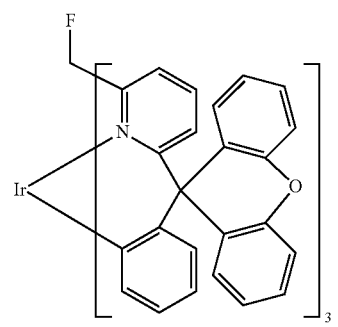 (141)
-continued
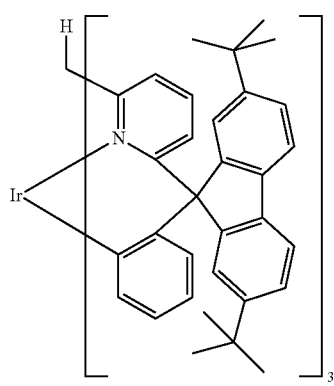 (142)
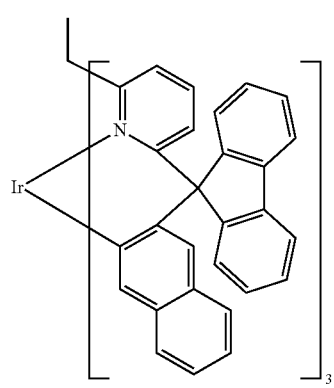 (143)
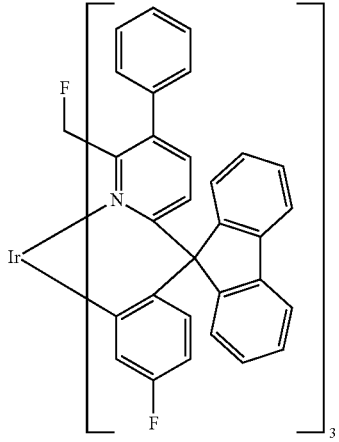 (144)
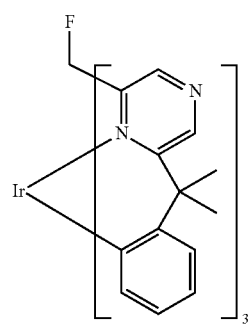 (145)

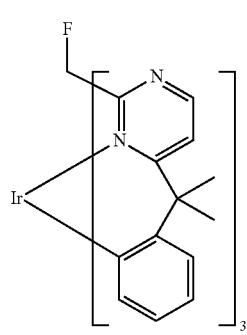
(146)
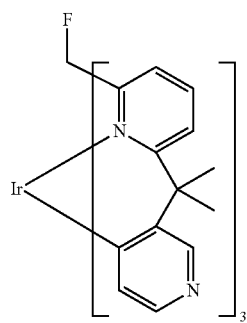
(147)
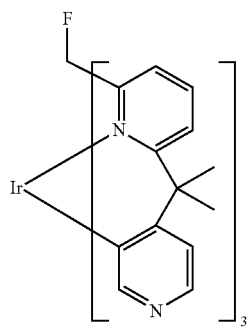
(148)
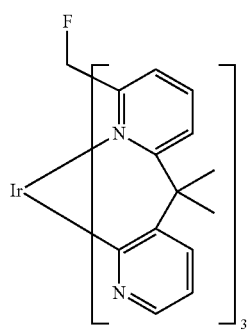
(149)
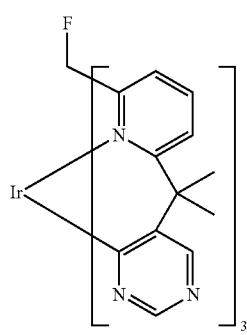
(150)
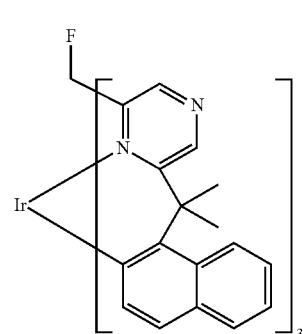
(151)
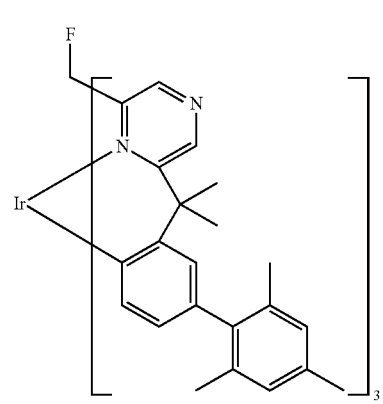
(152)
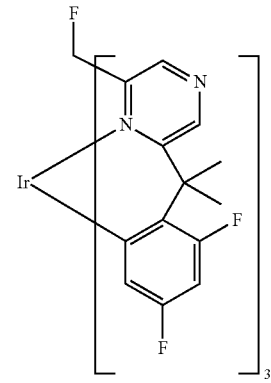
(153)
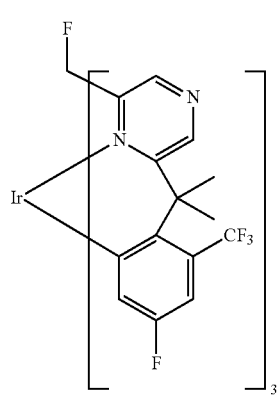
(154)

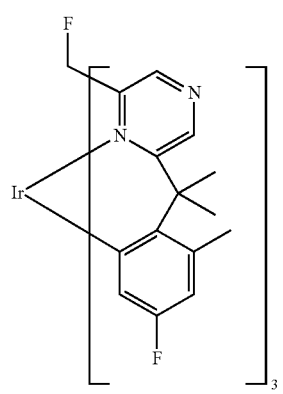
(155)
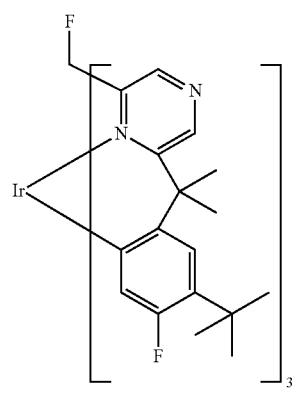
(156)
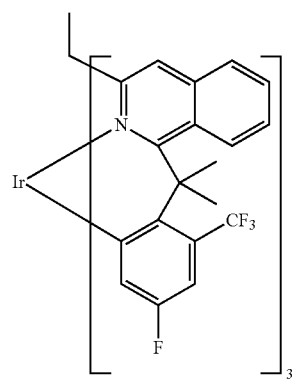
(157)
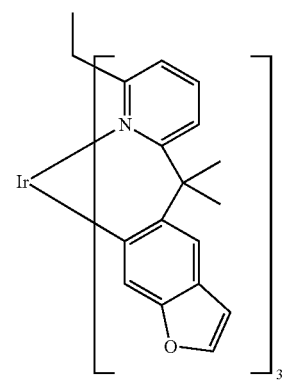
(158)
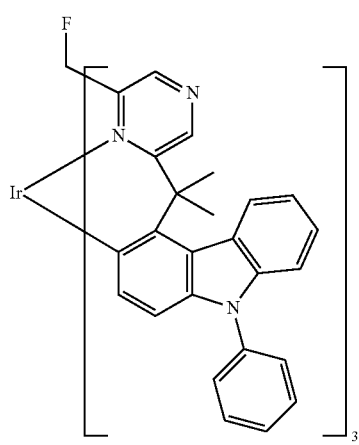
(159)
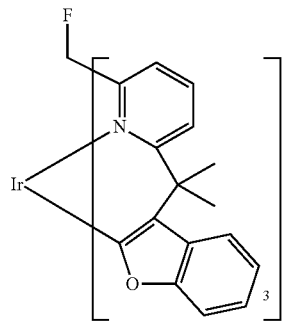
(160)
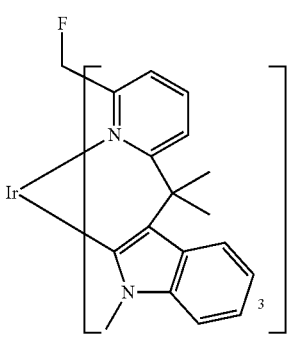
(161)
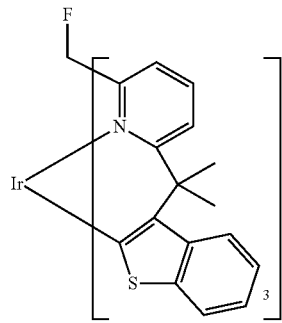
(162)

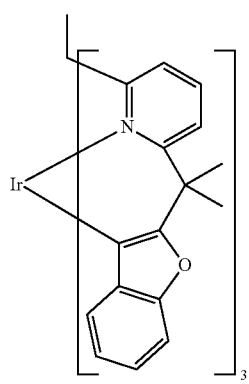
(163)
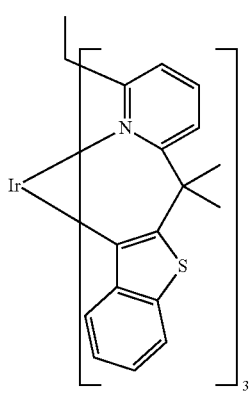
(164)
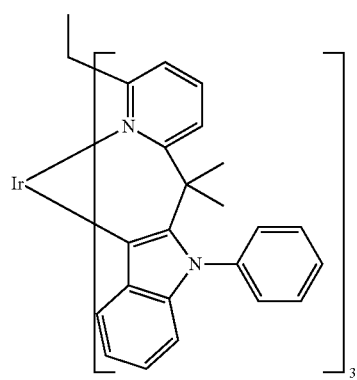
(165)
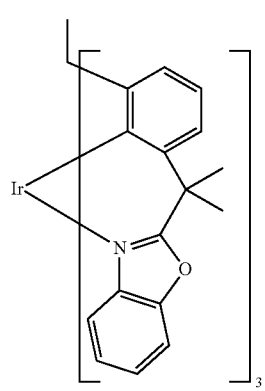
(166)
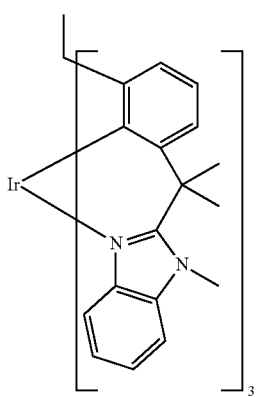
(167)
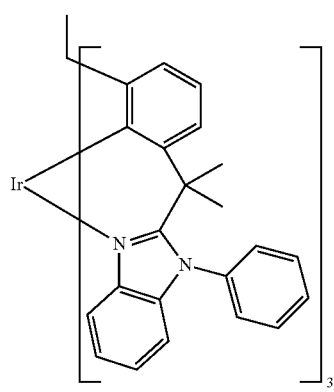
(168)
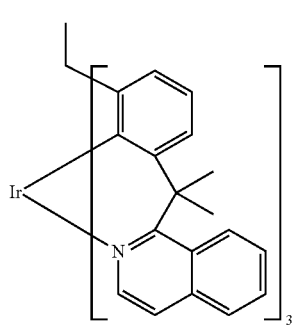
(169)
(170)

(171) 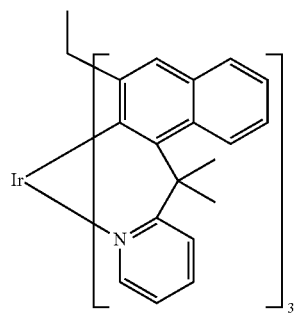
(172) 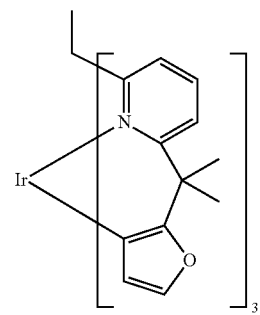
(173) 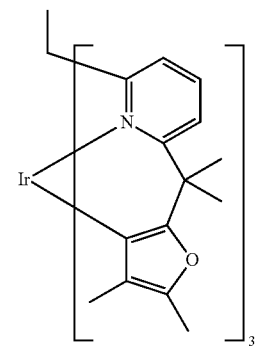
(174) 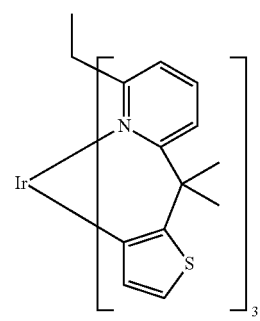
(175) 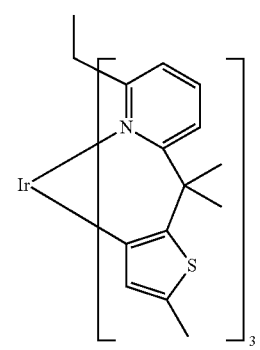
(176) 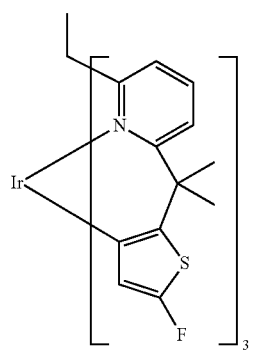
(177) 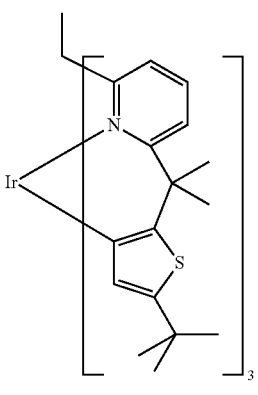
(178) 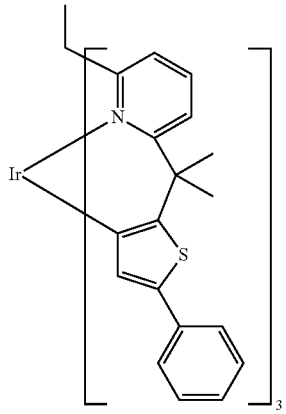
(179) 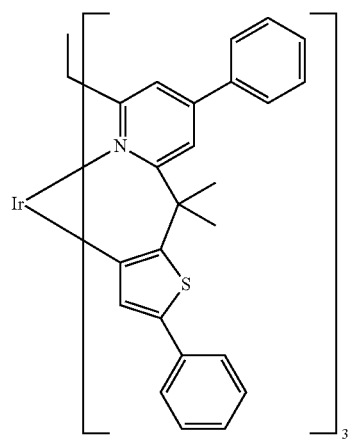

(180)
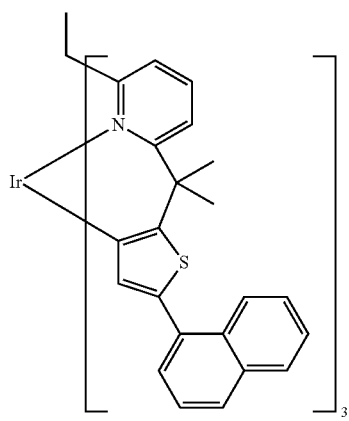
(181)
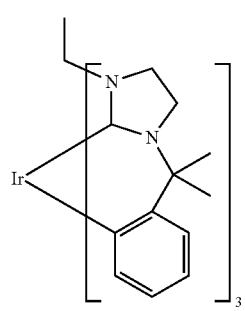
(182)
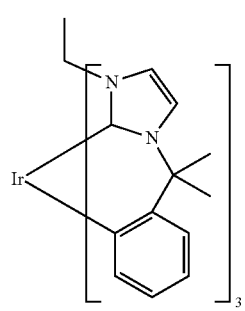
(183)
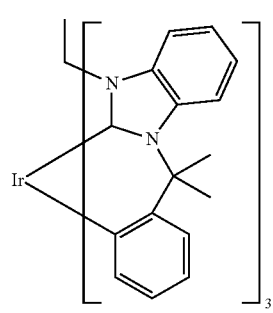
(184)
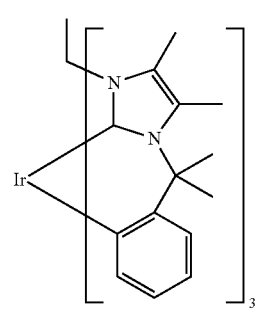
(185)
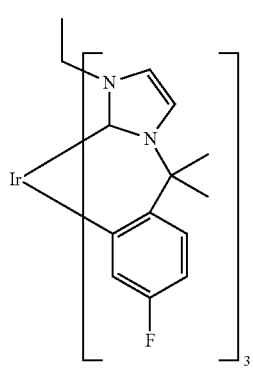
(186)
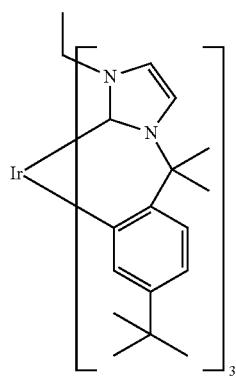
(187)
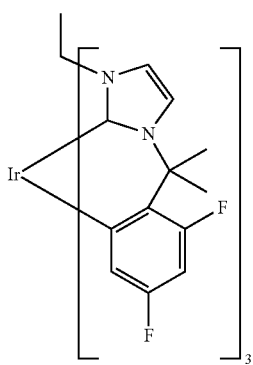
(188)
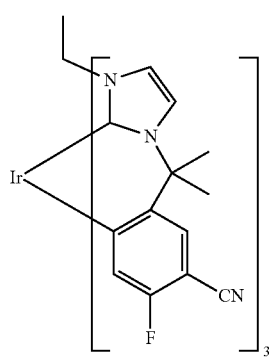

(189) 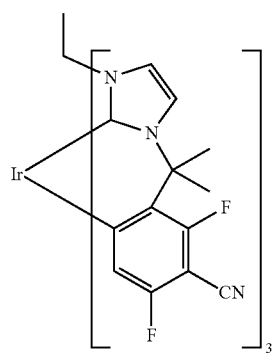
(190) 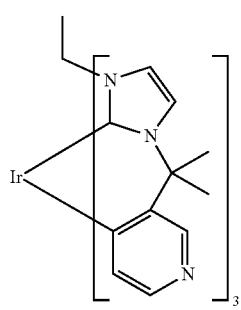
(191) 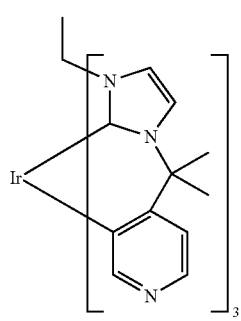
(192) 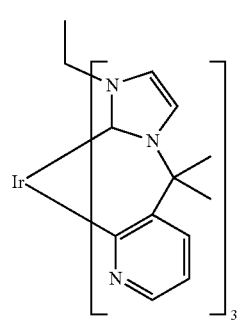
(193) 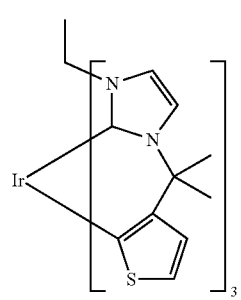
(194) 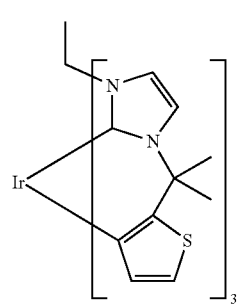
(195) 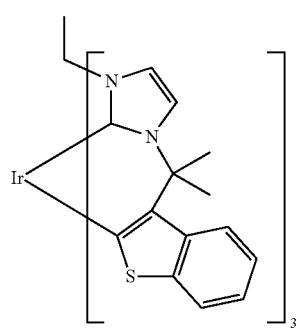
(196) 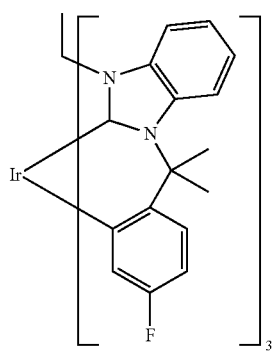
(197) 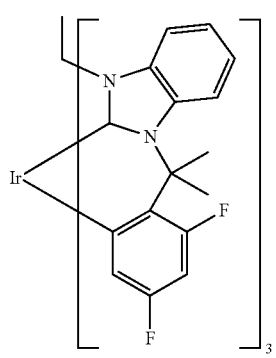

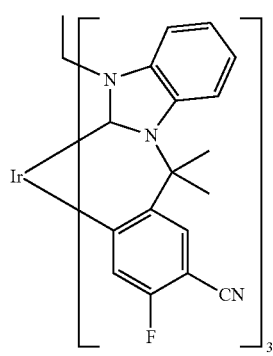
(198)
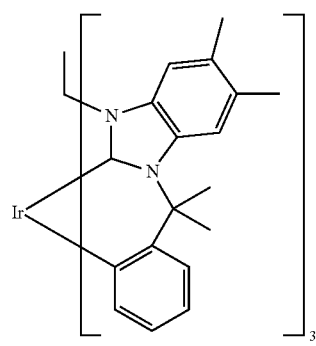
(199)
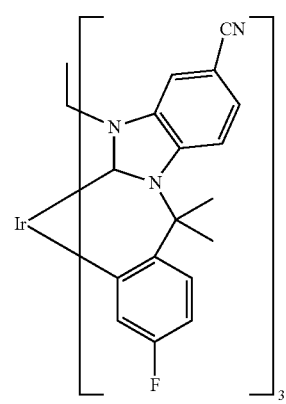
(200)
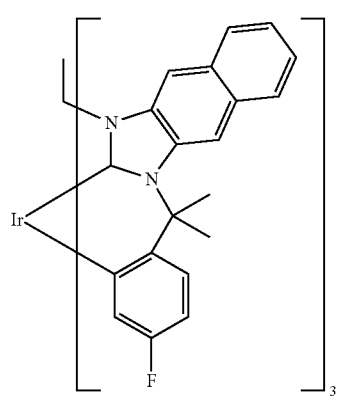
(201)
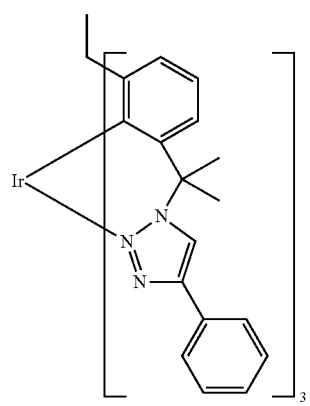
(202)
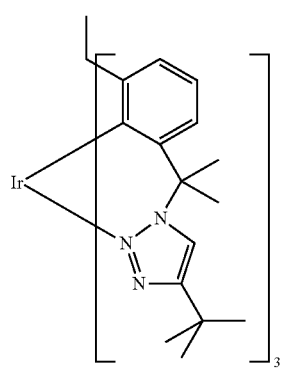
(203)
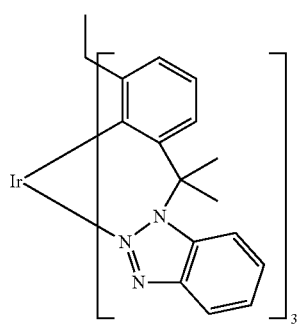
(204)
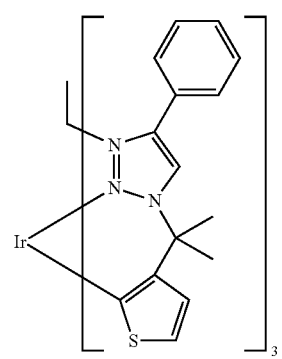
(205)

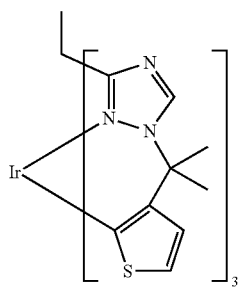
(206)
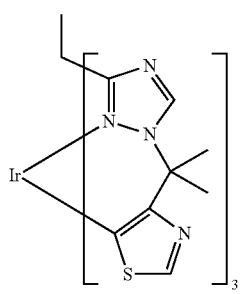
(207)
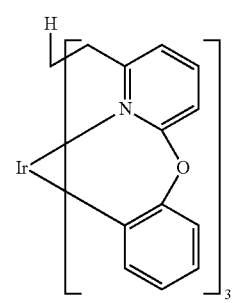
(208)
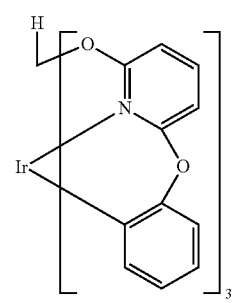
(209)
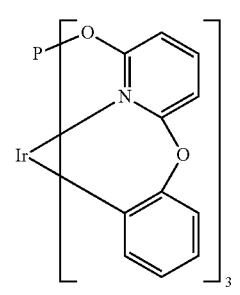
(210)
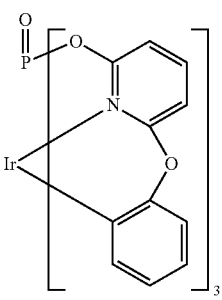
(211)
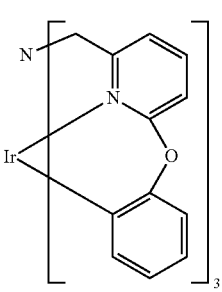
(212)
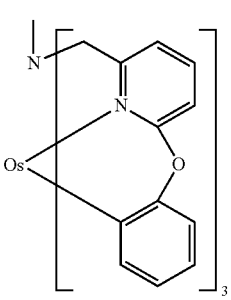
(213)
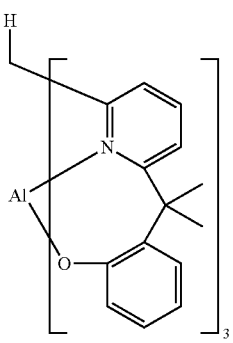
(214)
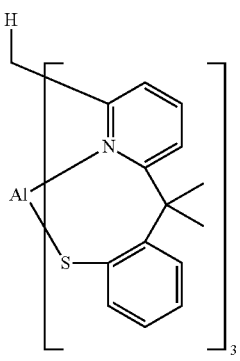
(215)

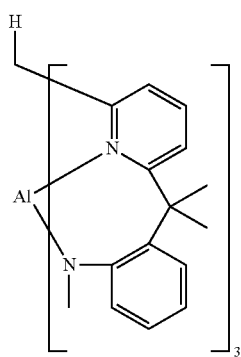
(216)
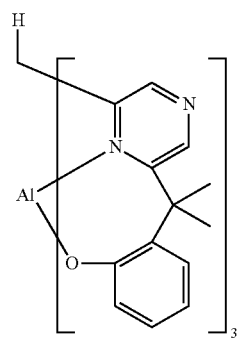
(217)
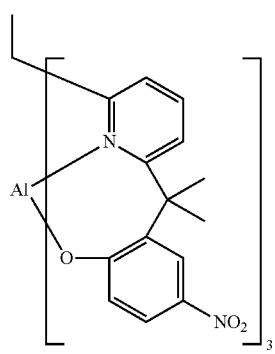
(218)
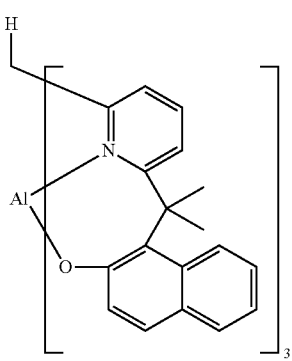
(219)
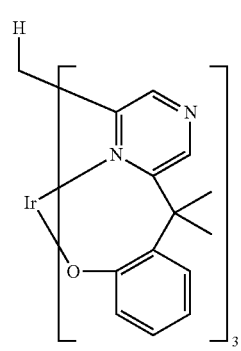
(220)
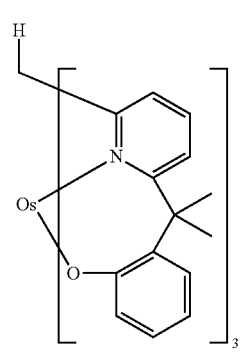
(221)
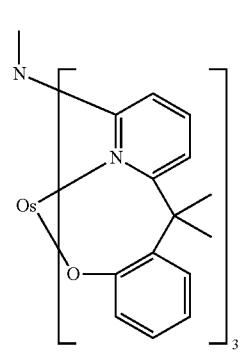
(222)
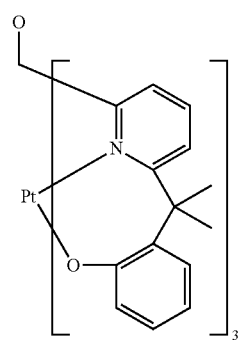
(223)

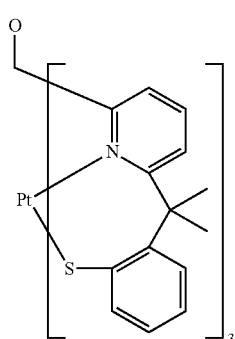 (224)
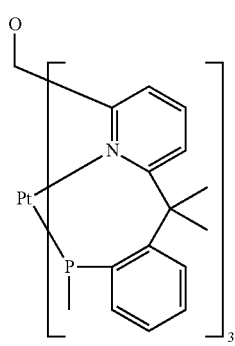 (225)
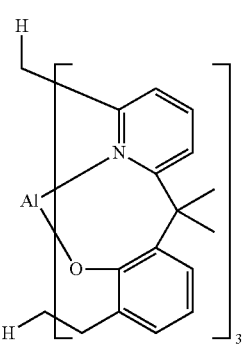 (226)
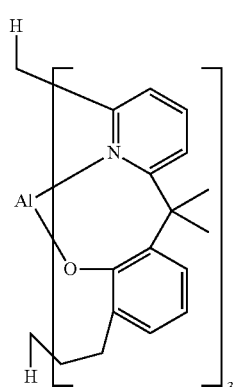 (227)
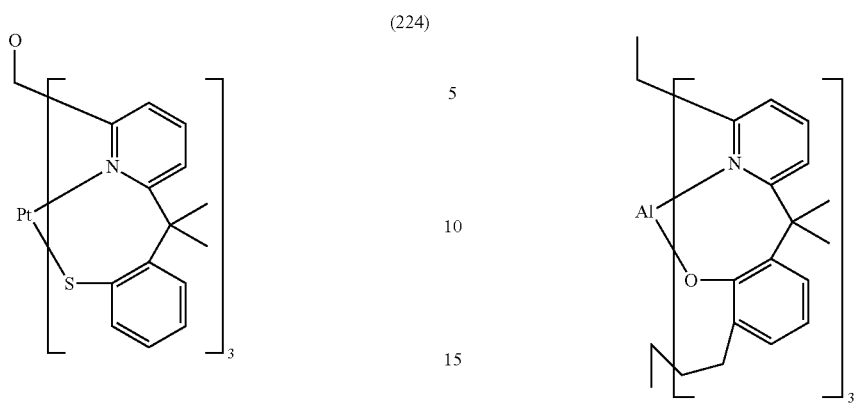 (228)
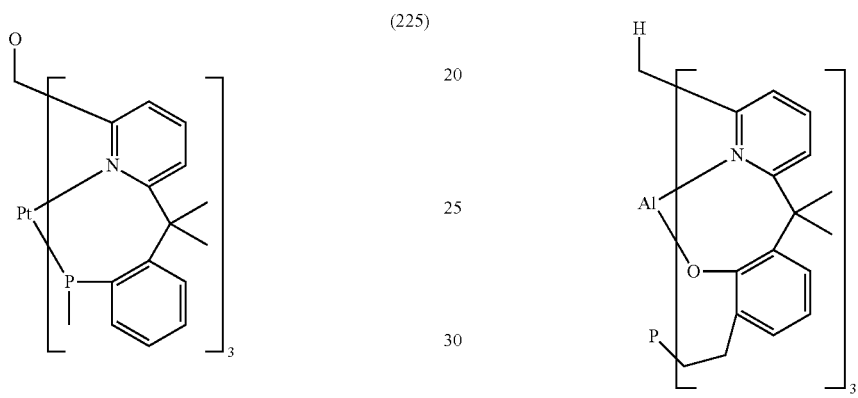 (229)
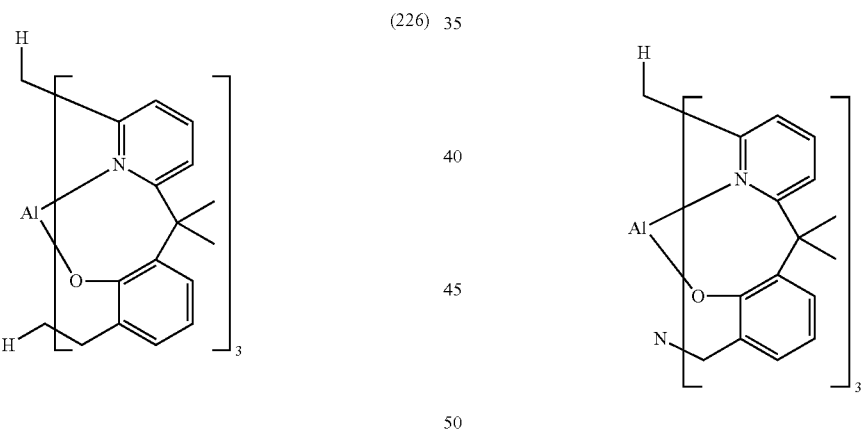 (230)
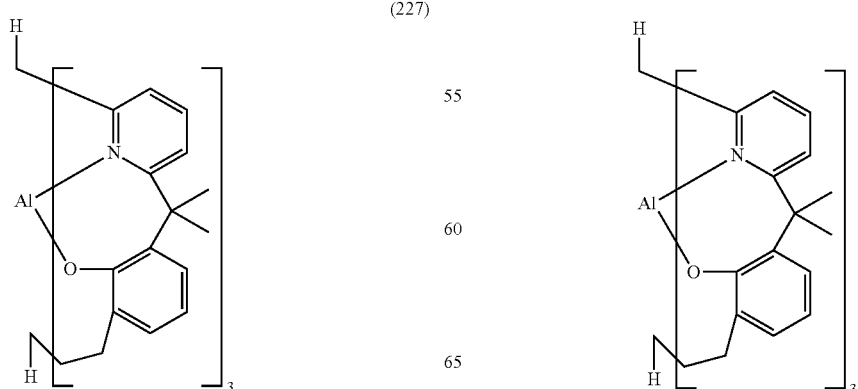 (231)

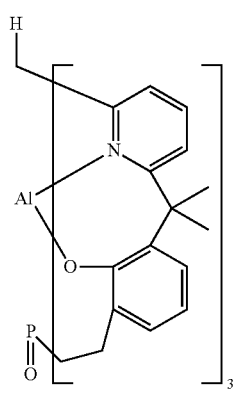
(232)
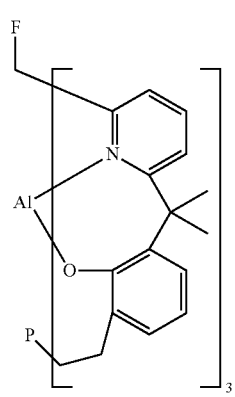
(233)
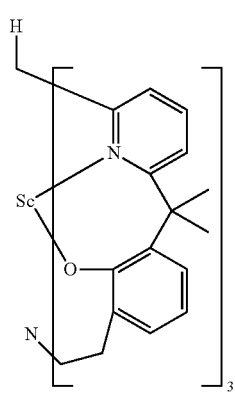
(234)
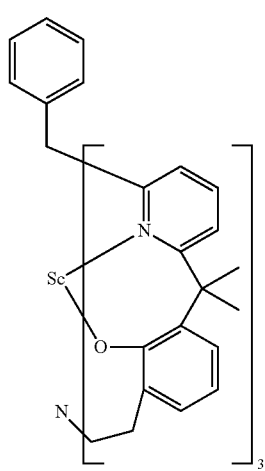
(235)
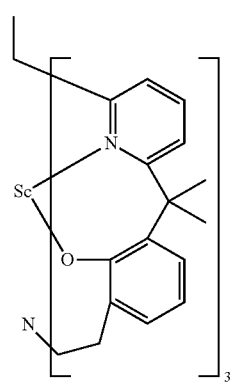
(236)
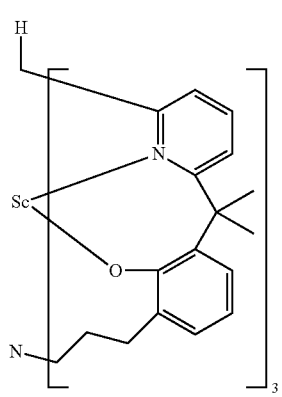
(237)
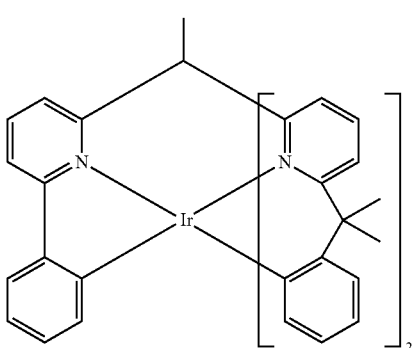
(238)
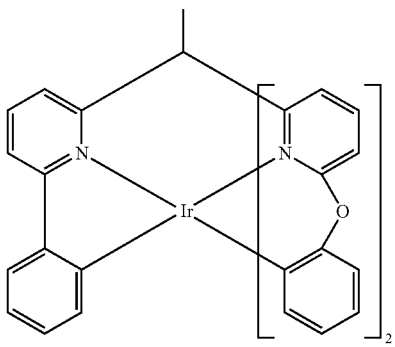
(239)

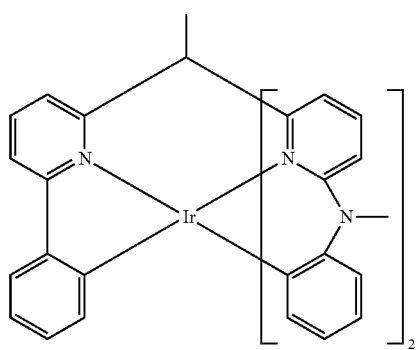
(240)
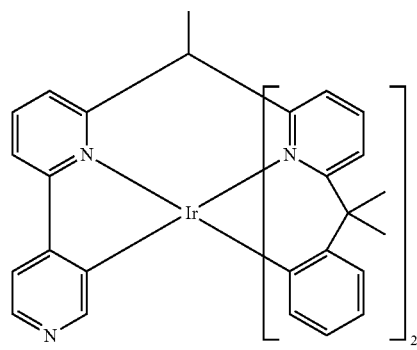
(244)
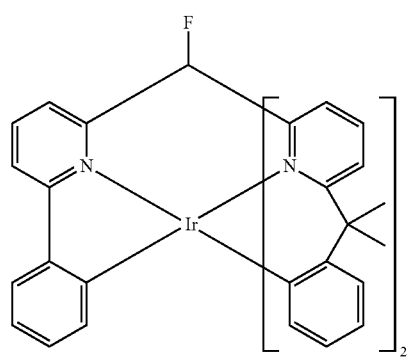
(241)
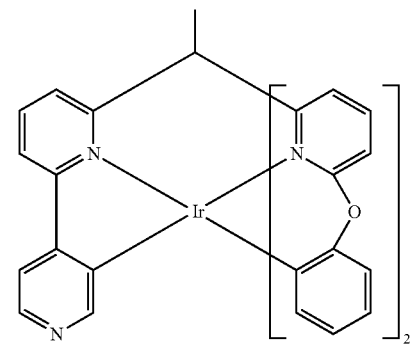
(245)
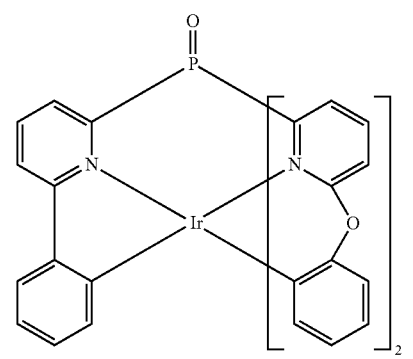
(242)
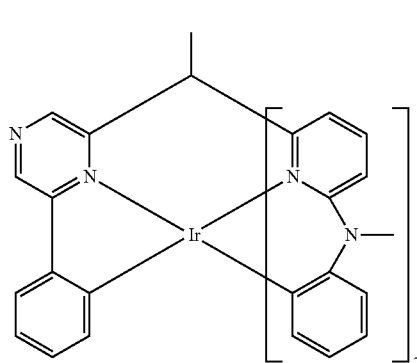
(246)
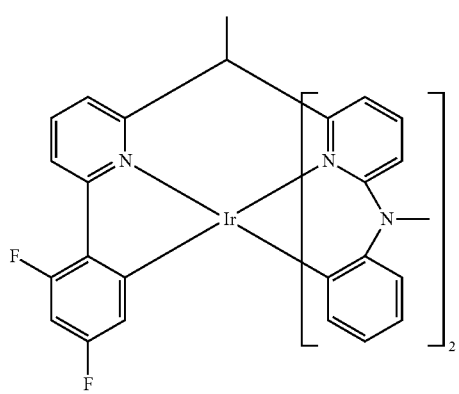
(243)
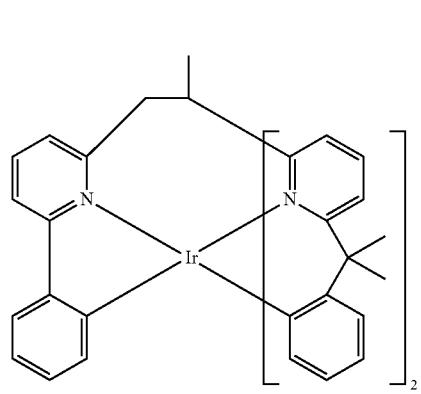
(247)

(248) 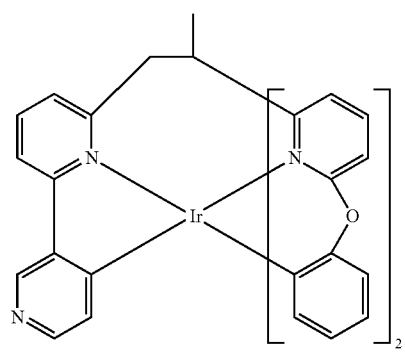
(249) 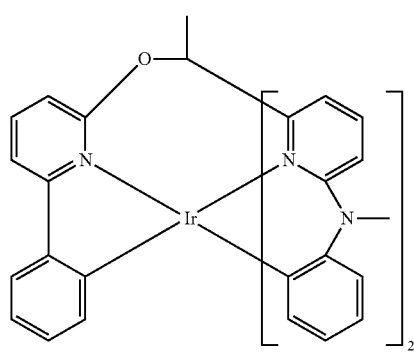
(250) 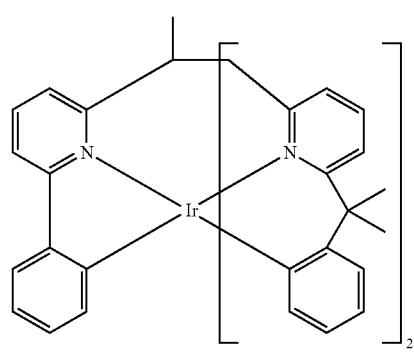
(251) 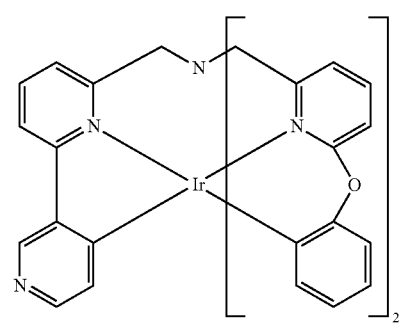
(252) 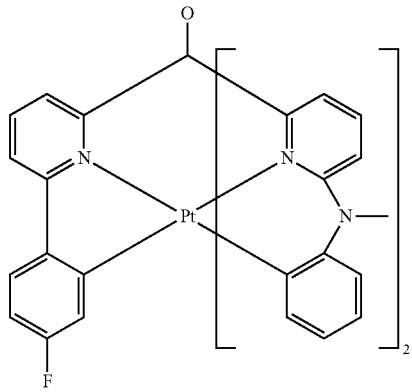
(253) 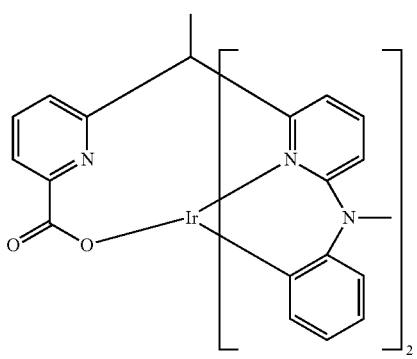
(254) 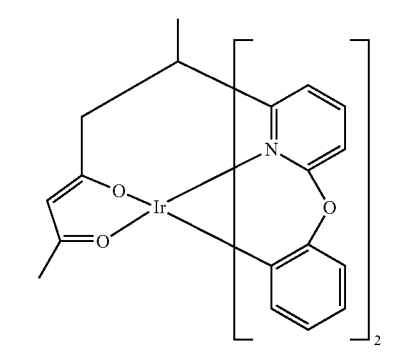
(255) 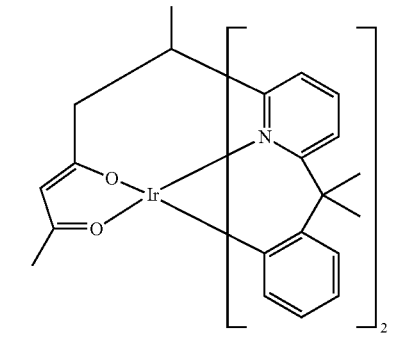

(256)
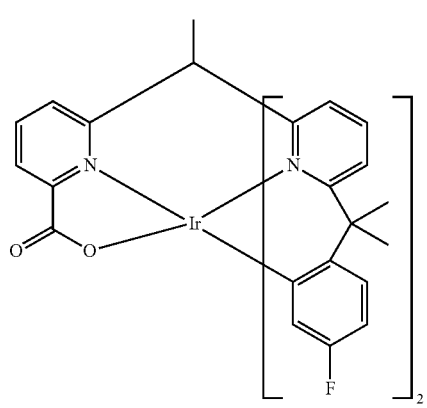
(257)
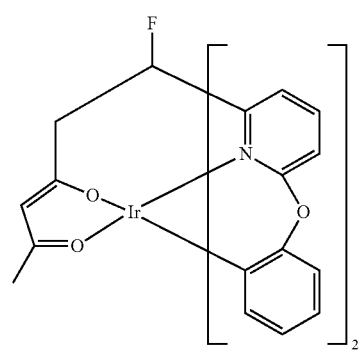
(258)
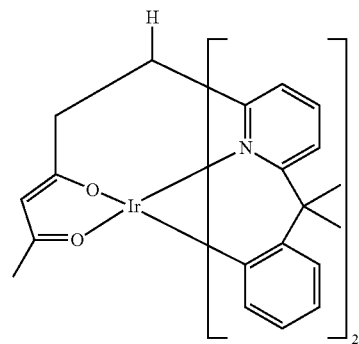
(259)
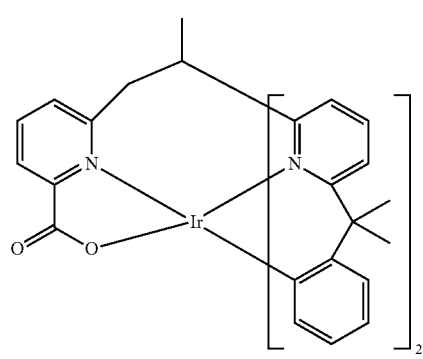
(260)
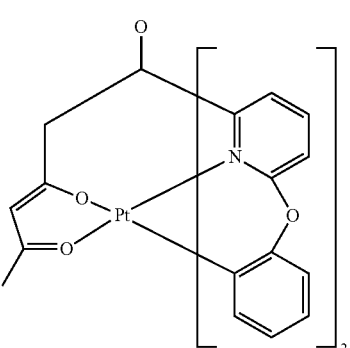
(261)
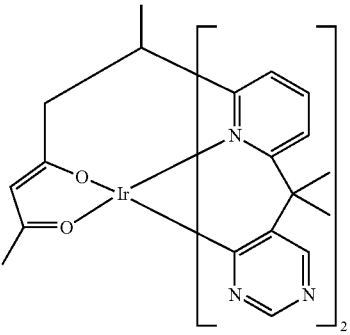
(262)
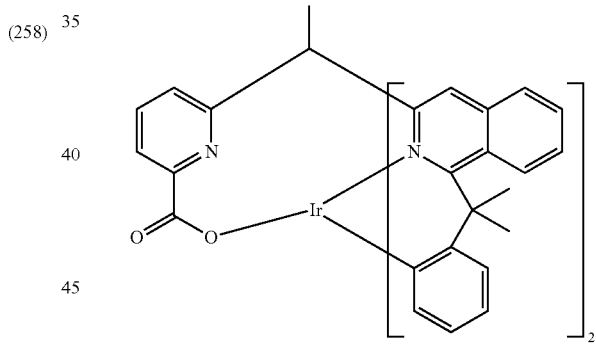
(263)
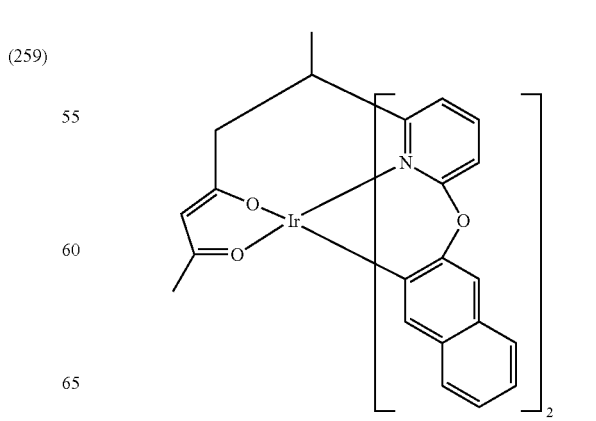

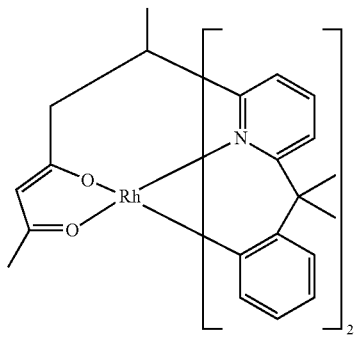

(264)

The compounds according to the invention described above, in particular compounds which are substituted by reactive leaving groups, such as bromine, iodine, boronic acid or boronic acid ester, can be used as monomers for the generation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (1), in which one or more bonds are present from the complex of the formula (1) to the polymer, oligomer or dendrimer. Depending on the linking of the compound of the formula (1), the complex therefore forms a side chain of the oligomer or polymer or is linked in the main chain. The polymers, oligomers or dendrimers may be conjugated, partially conjugated or non-conjugated. The oligomers or polymers may be linear, branched or dendritic.

The same preferences as described above apply to the recurring units of the formula (1) in oligomers, dendrimers and polymers.

For the preparation of oligomers or polymers, the monomers according to the invention are homopolymerised or copolymerised with further monomers. Preference is given to copolymers in which the units of the formula (1) are preferably present to the extent of 0.01 to 50 mol %, particularly preferably in the range from 0.1 to 20 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The proportion of these units overall is preferably in the region of at least 50 mol %. The polymers, oligomers and dendrimers may also comprise further units, for example hole-transport units, in particular those based on triarylamines, and/or electron-transport units.

Furthermore, the metal complexes according to the invention may also be further functionalised and thus converted into extended metal complexes. An example which may be mentioned here is the functionalisation with arylboronic acids by the SUZUKI method or with primary or secondary amines by the HARTWIG-BUCHWALD method.

The complexes according to the invention described above, or oligomers, polymers or dendrimers comprising these complexes, are used as active component in electronic components, such as, for example, organic electroluminescent devices (=Organic light-emitting diodes, OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or also organic laser diodes (O-lasers).

Active components are, for example, charge-injection, charge-transport or charge-blocking materials, but in particular emission materials and matrix materials. For these functions, the compounds according to the invention exhibit particularly good properties, in particular as emission material, as already explained in the introduction and described in greater detail below.

The invention thus furthermore relates to the use of the compounds of the formula (1) in organic electronic components.

The invention furthermore relates to organic electronic components, such as, for example, organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (OLEDs, PLEDs), comprising one or more compounds of the formula (1). Preference is given to organic electronic components comprising one or more complexes which have a moiety of the formula (11) or in particular moieties of the formulae (15) to (30), where the preferences mentioned above for the compounds of the formula (1) also apply to the electronic components.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers (Charge-Generation Layers, IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). It is likewise possible for interlayers which have, for example, an exciton-blocking function to be introduced between two emitting layers. However, it should be pointed out that each of these layers does not necessarily have to be present.

In a preferred embodiment of the invention, the compound of the formula (1) is employed as emitting compound in an emitting layer. This is the case, in particular, if the metal M is a transition metal, in particular iridium or platinum. The organic electroluminescent device here may comprise one emitting layer or it may comprise a plurality of emitting layers, where at least one emitting layer comprises at least one compound of the formula (1). If a plurality of emission layers is present, these preferably have overall a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure, see, for example, WO 05/011013).

If the compound of the formula (1) is employed as emitting compound in an emitting layer, it is preferably employed in combination with one or more matrix materials. The mixture of the compound of the formula (1) and the matrix material comprises between 1 and 99% by weight, preferably between 2 and 90% by weight, particularly preferably between 3 and 40% by weight, in particular between 5 and 15% by weight, of the compound of the formula (1), based on the mixture as a whole comprising emitter and matrix material. Correspondingly, the mixture comprises between 99 and 1% by weight, preferably between 98 and 10% by weight, particularly preferably between 97 and 60% by weight, in particular between 95 and 85% by weight, of the matrix material, based on the mixture as a whole comprising emitter and matrix material.

Preferred matrix materials are CBP (N,N-biscarbazolylbiphenyl), carbazole derivatives (for example in accordance with WO 05/039246, US 2005/0069729, JP 2004/288381), azacarbazoles (for example in accordance with EP 1617710, EP 1617711, EP 1731584, JP 2005/347160), ketones (for example in accordance with WO 04/093207), phosphine oxides, sulfoxides and sulfones (for example in accordance with WO 05/003253), oligophenylenes, aromatic amines (for example in accordance with US 2005/0069729), bipolar matrix materials (for example in accordance with WO 07/137,725) or silanes (for example in accordance with WO 05/111172). Also suitable as matrix materials are the compounds according to the invention mentioned below.

In a further preferred embodiment of the invention, the compound of the formula (1) is employed as matrix material for an emitting compound in an emitting layer. This is the case, in particular, if the metal M is a main-group metal, in particular aluminium, gallium or indium. The organic electroluminescent device here may comprise one emitting layer or it may comprise a plurality of emitting layers, where at least one emitting layer comprises at least one compound of the formula (1) as matrix material. If a plurality of emission layers is present, the comments made above apply to these.

If the compound of the formula (1) is employed as matrix material for an emitting compound in an emitting layer, it is preferably employed in combination with one or more phosphorescent materials (triplet emitters). For the purposes of this invention, phosphorescence is taken to mean luminescence from an excited state with relatively high spin multiplicity, i.e. a spin state >1, in particular from an excited triplet state. For the purposes of this invention, all luminescent iridium and platinum complexes are intended to be taken to mean phosphorescent compounds. The mixture of the compound of the formula (1) and the emitting compound then comprises between 99 and 1% by weight, preferably between 98 and 10% by weight, particularly preferably between 97 and 60% by weight, in particular between 95 and 85% by weight, of the compound of the formula (1), based on the mixture as a whole comprising emitter and matrix material. Correspondingly, the mixture comprises between 1 and 99% by weight, preferably between 2 and 90% by weight, particularly preferably between 3 and 40% by weight, in particular between 5 and 15% by weight, of the emitter, based on the mixture as a whole comprising emitter and matrix material.

Suitable phosphorescent compounds triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614 and WO 05/033244. Furthermore, suitable emitters are the compounds according to the invention mentioned above. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without an inventive step.

In a further preferred embodiment of the invention, the compound of the formula (1) is employed as hole-blocking material in a hole-blocking layer and/or as electron-transport material in an electron-transport layer. This is the case, in particular, if the metal M is a main-group metal, in particular aluminium, gallium or indium. The emitting layer here may be fluorescent or phosphorescent.

Preference is furthermore given to an organic electroluminescent device, characterised in that one or more layers are applied by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are applied by means of the OVPD (organic vapour phase deposition) process or with the aid of carriergas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, for example, by suitable substitution, are necessary for this purpose.

These processes are generally known to the person skilled in the art and can be applied by him without problems to organic electroluminescent devices comprising compounds of the formula (1).

The compounds according to the invention and the organic electroluminescent devices produced therewith are distinguished by the following surprising advantages over the prior art:

1. In contrast to many metal complexes in accordance with the prior art, which undergo partial or complete pyrolytic decomposition on sublimation, the compounds according to the invention have high thermal stability.
2. Organic electroluminescent devices comprising compounds of the formula (1) as emitting materials have an excellent lifetime.
3. Blue-phosphorescing complexes which have a deep-blue emission colour and a long lifetime on use in organic electroluminescent devices are accessible. This is a significant advance over the prior art, since blue-phosphorescing devices were hitherto only accessible with poor colour coordinates and in particular a very poor lifetime.

4. The compounds according to the invention, employed in organic electroluminescent devices, result in high efficiencies and in steep current-voltage curves.

These above-mentioned advantages are not accompanied by an impairment of the other electronic properties.

The invention is explained in greater detail by the following examples, without wishing to restrict it thereby. The person skilled in the art will be able to prepare further complexes according to the invention from the descriptions without an inventive step and use them in organic electronic devices or use the process according to the invention.

EXAMPLES

The following syntheses are carried out under a protective-gas atmosphere in dried solvents, unless indicated otherwise. The solvents and reagents can be purchased from ALDRICH or ABCR. The precursors can be prepared as follows: tris(2-bromo-6-pyridyl)phosphine and tris(2-bromo-6-pyridyl)methanol in accordance with WO 98/22148; tris(2-bromo-6-pyridyl)phosphine oxide, tris(2-bromo-6-pyridyl)fluoromethane and tris(2-methyl-6-pyridyl)fluoromethane in accordance with WO 04/081017; tris(2-methyl-6-pyridyl)phosphine in accordance with *Heteroatomic Chemistry* 1990, 1(4), 295; tris(2-methyl-6-pyridyl)phosphine oxide in accordance with *Heteroatomic Chemistry* 1997, 8(5), 439; tris(2-methyl-6-pyridyl)-methane in accordance with *J. Am. Chem. Soc.* 1999, 121(47), 11007; 1,1,1-tris(2-methyl-6-pyridyl)ethane in accordance with *Inorg. Chem.* 2003, 42(4), 11993; tris((2-methyl-6-pyridyl)methanol in accordance with *Tetrahedron Letters* 1998, 39(46), 8509; tris(2-bromo-6-pyridyl)methyl methyl ether and analogously tris(2-methyl-6-pyridyl)methyl methyl ether in accordance with *Inorg. Chem.* 2000, 39(2), 226; sodium dichloro-bis-acetylacetonatoiridate (III) in accordance with WO 06/018202.

Example 1

Synthesis of tris(2-(phenylmethyl)-6-pyridyl)methyl methyl ether

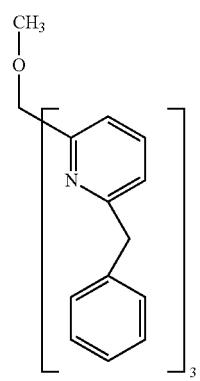

The synthesis is carried out analogously to *Organometallics* 2007, 26(17), 4105. 5.88 g (17 mmol) of Zn(tmp)$_2$ are added to a solution of 3.19 g (10 mmol) of tris(2-methyl-6-pyridyl)methane methyl ether in 100 ml of toluene, and the mixture is subsequently stirred at 50° C. for 20 h. 5.5 g (35 mmol) of bromotoluene and a catalyst solution, prepared separately in advance from 121 mg (0.6 mmol) of tri-tert butylphosphine and 275 mg (0.3 mmol) of Pd$_2$(dba)$_3$ in 5 ml of toluene, are added to this solution. The mixture is subsequently stirred at room temperature for a further 24 h, 100 ml of saturated ammonium chloride solution are then added, and the organic phase is separated off, washed twice with 100 ml of water each time, dried over magnesium sulfate and then evaporated to dryness. The residue is recrystallised from acetone/ethanol. Yield: 3.75 g, 68.5%; purity: 98.0% according to NMR.

The following compounds are prepared analogously starting from the corresponding methylpyridine and the corresponding aryl bromide:

| Ex. | Starting material | Product | Yield |
|---|---|---|---|
| 2 | [structure: tris(2-methyl-6-methylpyridyl)] | [structure: tris(2-methyl-6-benzylpyridyl)] | 51.9% |
| 3 | [structure: fluoro analog starting material] | [structure: fluoro analog product] | 37.5% |
| 4 | [structure: phosphine oxide starting material] | [structure: phosphine oxide product] | 52.0% |

-continued

| Ex. | Starting material | Product | Yield |
|---|---|---|---|
| 5 | (2-ethyl-6-methylpyridine) | (tris product with p-tolyl) | 71.7% |
| 6 | (2-ethyl-6-methylpyridine) | (tris product with naphthyl) | 74.8% |

Example 7

Synthesis of tris(2-(phenoxy)-6-pyridyl)fluoromethane

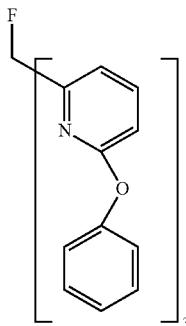

The synthesis is carried out analogously to Tetrahedron Letters 2006, 47(29), 5045. A suspension of 5.02 g (10 mmol) of tris(2-bromo-6-pyridyl)-fluoromethane, 5.65 g (60 mmol) of phenol, 29.32 g (90 mmol) of caesium carbonate and 64 mg (1 mmol) of copper powder in 100 ml of DMF is treated in the microwave (60 watts) at 100° C. for 15 min. After cooling, 500 ml of dichloromethane are added to the suspension, which is then washed five times with 300 ml of water each time, dried over magnesium sulfate and then evaporated in vacuo. The glass-like residue is chromatographed on silica gel with dichloromethane/hexane (1:4, v/v). Yield: 3.10 g, 56.6%; purity: about 98.0% according to NMR.

The following compounds are prepared analogously starting from the corresponding bromopyridine and the corresponding phenols or thiophenols:

| Ex. | Starting material | Product | Yield |
|---|---|---|---|
| 8 | (2-methoxymethyl-6-bromopyridine) | (with phenoxy) | 55.8% |
| 9 | (2-fluoromethyl-6-bromopyridine) | (with 2-fluorophenoxy) | 41.8% |
| 10 | (2-fluoromethyl-6-bromopyridine) | (with 2-naphthoxy) | 36.1% |
| 11 | (2-hydroxymethyl-6-bromopyridine) | (with phenoxy) | 43.3% |

| Ex. | Starting material | Product | Yield |
|---|---|---|---|
| 12 | | | 51.0% |
| 13 | | | 50.8% |
| 14 | | | 27.0% |
| 15 | | | 29.3% |

Example 16

Synthesis of tris(2-(diphenylamino)-6-pyridyl)fluoromethane

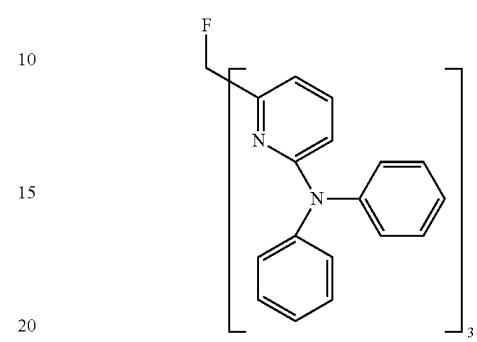

6.77 g (40 mmol) of diphenylamine, 7.69 g (80 mmol) of sodium tert-butoxide, 121 mg (0.6 mmol) of tri-tert-butylphosphine and 67 mg (0.3 mmol) of palladium(II) acetate are added to a solution of 5.02 g (10 mmol) of tris(2-bromo-6-pyridyl)fluoromethane in 100 ml of toluene, and the mixture is subsequently stirred at 100° C. for 4 h. After cooling, 100 ml of saturated ammonium chloride solution are added, and the organic phase is separated off, filtered through silica gel, washed twice with 100 ml of water each time, dried over magnesium sulfate and then evaporated to dryness. The residue is recrystallised from acetone/ethyl acetate (1:2, v/v). Yield: 4.50 g, 58.5%; purity: about 98.0% according to NMR.

The following compounds are prepared analogously starting from the corresponding bromopyridine and the corresponding arylamines:

| Ex. | Starting material | Product | Yield |
|---|---|---|---|
| 17 | | | 56.1% |
| 18 | | | 51.0% |

-continued

| Ex. | Starting material | Product | Yield |
|---|---|---|---|
| 19 | [structure: 2-bromo-6-(hydroxymethyl)pyridine]₃ | [structure: product with N(4-fluorophenyl)₂]₃ | 47.3% |
| 20 | [structure: 2-bromo-6-(hydroxymethyl)pyridine]₃ | [structure: product with N-naphthyl amine]₃ | 26.7% |
| 21 | 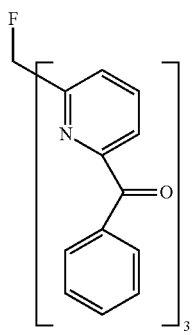 | [structure: product with N-methyl-N-naphthyl amine]₃ | 33.5% |

Example 22

Synthesis of tris(2-(benzoyl)-6-pyridyl)fluoromethane

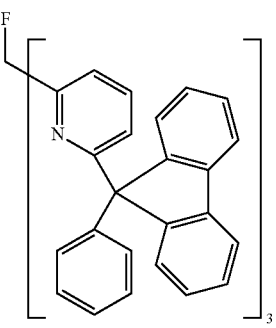

13.2 ml (33 mmol) of n-butyllithium (2.5 M in hexane) are added at −78° C. to a solution of 5.02 g (10 mmol) of tris(2-bromo-6-pyridyl)fluoromethane in 200 ml of THF, the mixture is stirred for a further 2 h, and a mixture of 4.13 g (40 mmol) of benzonitrile in 50 ml of THF is then added dropwise. After slow warming to room temperature, the THF is removed in vacuo, the residue is taken up in 100 ml of NMP, 10 ml of water and 2 ml of acetic acid are added, and the mixture is then heated under reflux for 1 h. After the mixture has been cooled to 60° C., 100 ml of 5% potassium carbonate solution are added dropwise, and the mixture is stirred for a further 30 min. The solid is filtered off with suction, washed three times with 50 ml of water each time and twice with 100 ml of methanol each time and, after drying, finally recrystallised from acetone/ethanol (1:2, v/v). Yield: 3.93 g, 68.1%; purity: about 98.0% according to NMR.

Example 23

Synthesis of tris(2-(9-phenylfluoren-9-yl)-6-pyridyl)-fluoromethane

[structure]

A Grignard reagent is prepared from 8.16 g (35 mmol) of 2-bromobiphenyl and 0.85 g (35 mmol) of magnesium in a mixture of 50 ml of THF and 10 ml of 1,2-dimethoxyethane and is subsequently added dropwise to a solution of 5.78 g (10 mmol) of tris(2-(benzoyl)-6-pyridyl)fluoromethane in 200 ml of THF at room temperature. After the mixture has been stirred for a further 3 h, the THF is removed in vacuo, and the residue is dissolved in 100 ml of glacial acetic acid. 5 ml of acetic anhydride and 0.5 ml of conc. sulfuric acid are added to the solution, and the mixture is heated under reflux for 3 h and then freed from the glacial acetic acid in vacuo. The residue is suspended in 300 ml of dichloromethane and rendered alkaline by addition of saturated potassium carbonate solution. The organic phase is separated off, washed three times with water, dried over magnesium sulfate and then evaporated in vacuo. The glass-like residue is chromatographed on silica gel with dichloromethane/hexane (1:5, v/v). Yield: 3.86 g, 39.1%; purity: about 98.0% according to NMR.

Example 24

Synthesis of tris(2-(2-hydroxyphenylmethyl)-6-pyridyl)-fluoromethane

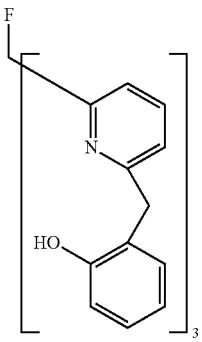

The synthesis is carried out analogously to Organometallics 2007, 26(17), 4105-4108. 5.88 g (17 mmol) of Zn(tmp)$_2$ are added to a solution of 3.07 g (10 mmol) of tris(2-methyl-6-pyridyl)fluoromethane in 100 ml of toluene, and the mixture is subsequently stirred at 50° C. for 20 h. 9.00 g (35 mmol) of 2-(2-bromophenoxy)tetrahydropyran and a catalyst solution, prepared separately in advance from 121 mg (0.6 mmol) of tri-tert-butylphosphine and 275 mg (0.3 mmol) of Pd$_2$(dba)$_3$ in 5 ml of toluene, are added to this solution. The mixture is subsequently stirred at room temperature for a further 24 h, 100 ml of saturated ammonium chloride solution are then added, and the organic phase is separated off, washed twice with 100 ml of water each time, dried over magnesium sulfate and then evaporated to dryness. The residue is taken up in 100 ml of THF, 10 ml of water and 1 ml of conc. HCl are added, and the mixture is stirred at 50° C. for 6 h and, after cooling, adjusted to pH=10-11 using saturated potassium carbonate solution. After the aqueous phase has been separated off and the organic phase has been dried using saturated sodium chloride solution, the THF is removed in vacuo. The residue is recrystallised from ethyl acetate/methanol (1:2). Yield: 3.88 g, 66.5%; purity: about 98.0% according to NMR.

Example 25

Synthesis of bis(2-(2-(diphenylamino))-6-pyridyl)-(2-phenyl-6-pyridyl)methanol

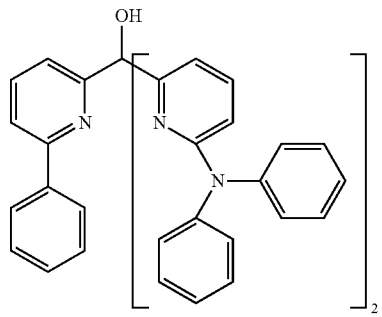

42.3 g (250 mmol) of diphenylamine, 48.1 g (500 mmol) of sodium tert-butoxide, 404 mg (2 mmol) of tri-tert-butylphosphine and 225 mg (1 mmol) of palladium(II) acetate are added to a solution of 34.2 g (100 mmol) of bis(2-bromo-6-pyridyl) ketone in 1000 ml of toluene, and the mixture is subsequently stirred at 100° C. for 4 h. After the mixture has been cooled, 1000 ml of saturated ammonium chloride solution are added, and the organic phase is separated off, filtered through silica gel, washed twice with 1000 ml of water each time, dried over magnesium sulfate and then evaporated to dryness. The residue is recrystallised from ethanol/ethyl acetate (8:1, v/v). Yield: 39.5 g, 76.1%; purity: about 98.0% according to NMR.

20 ml (50 mmol) of n-butyllithium (2.5 M in hexane) are added dropwise to a suspension, cooled to −78° C., of 11.8 g (50 mmol) of 2,6-dibromopyridine in 300 ml of diethyl ether. When the addition is complete, the mixture is stirred for a further 60 min. A solution of 25.9 g (50 mmol) of bis(2-(diphenylamino)-6-pyridyl) ketone in 150 ml of THF is then rapidly added dropwise at such a rate that the temperature does not exceed −40° C. After the mixture has warmed to room temperature, 100 ml of water are added, and the organic phase is separated off, washed twice with 100 ml of water each time, dried over magnesium sulfate and then evaporated to dryness. The residue is recrystallised from ethanol/dichloromethane (10:1, v/v). Yield: 26.0 g, 76.9%; purity: about 98.0% according to NMR.

61 mg (0.30 mmol) of tri-tert-butylphosphine and then 56 mg (0.25 mmol) of palladium(II) acetate are added to a suspension of 16.9 g (25 mmol) of bis(2-(2-(diphenylamino))-6-pyridyl)-(2-bromo-6-pyridyl)methanol, 4.27 g (35 mmol) of phenylboronic acid and 8.72 g (150 mmol) of anhydrous potassium fluoride in 200 ml of THF, and the mixture is heated under reflux for 2 h. A mixture of 100 ml of ethanol and 200 ml of water is then added dropwise. After the mixture has cooled, the precipitated solid is filtered off with suction, washed three times with 50 ml of ethanol and recrystallised from ethanol/THF (10:1, v/v). Yield: 12.7 g, 75.4%; purity: about 98.0% according to NMR.

Example 26

Synthesis of iridium(III) complexes (Tris(2-(phenylmethyl)-6-pyridyl)methyl ether)iridium(III))

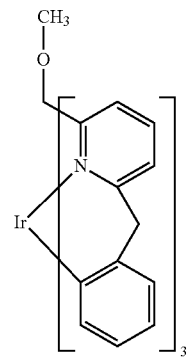

Method A:
A suspension of 2.74 g (5 mmol) of tris(2-(phenylmethyl)-6-pyridyl)methyl methyl ether and 2.42 g (5 mmol) of sodium dichlorobisacetylacetonatoiridate(III) in 20 ml of ethylene glycol is heated at 170° C. for 20 h. After cooling, the mixture is diluted with 100 ml of water, the aqueous phase is extracted three times with 50 ml of dichloromethane each time, the organic phase is dried over magnesium sulfate and evaporated, and the residue is chromatographed on silica gel with dichloromethane and finally recrystallised from dichloromethane/methanol. Yield: 1.23 g, 33.6%; purity: >99.5% according to NMR.

Method B:
A suspension of 2.74 g (5 mmol) of tris(2-(phenylmethyl)-6-pyridyl)methyl methyl ether and 1.49 g (5 mmol) of iridium(III) chloride hydrate in a mixture of 75 ml of 2-ethoxyethanol and 25 ml of water is heated under reflux for 20 h. After cooling, the mixture is diluted with 100 ml of water, and the precipitate is filtered off, washed three times with 20 ml of methanol and dried. The solid obtained in this way is suspended in 50 ml of diethylene glycol dimethyl ether, 2.57 g (10 mmol) of silver(I) trifluoromethanesulfonate are added, and the mixture is stirred at 110° C. for 5 h. After cooling, the mixture is diluted with 100 ml of water, the aqueous phase is extracted three times with 50 ml of dichloromethane each time, the organic phase is dried over magnesium sulfate and evaporated, and the residue is chromatographed on silica gel with dichloromethane and finally recrystallised from dichloromethane/methanol. Yield: 0.97 g, 21.0%; purity: >99.5% according to NMR.

The following metal complexes are prepared analogously starting from the corresponding ligand:

| Ex. | Starting material | Product | Yield |
|---|---|---|---|
| 27 | Example 7 | | Method A 37.3% |
| 28 | Example 17 | | Method A 59.0% |
| 29 | Example 19 | | Method B 43.1% |
| 30 | Example 23 | | Method A 51.5% |

-continued

| Ex. | Starting material | Product | Yield |
|---|---|---|---|
| 31 | Example 25 | | Method B 55.0% |
| 32 | | | Method A 31.0% |
| 33 | | | Method A 22.9% |
| 34 | | | Method A 17.8% |

Example 35

Synthesis of platinum(IV) complexes: Tris(2-(phenoxy)-6-pyridyl)methanolatoplatinum(IV)

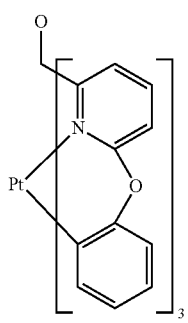

A suspension of 2.70 g (5 mmol) of tris(2-(phenoxy)-6-pyridyl)fluoromethane and 2.08 g (5 mmol) of potassium tetrachloroplatinate(II) in a mixture of 50 ml of acetic acid and 10 ml of water is heated under reflux for 48 h. After the mixture has cooled, the precipitate is filtered off, washed three times with 20 ml of water/ethanol (1:1, v/v) each time and three times with 20 ml of ethanol each time and then dried in vacuo. The residue is suspended in 300 ml of dichloromethane, a mixture of 0.80 g (5 mmol) of bromine in 50 ml of dichloromethane is added dropwise, the mixture is stirred at room temperature for 5 h, 2.57 g (10 mmol) of silver trifluoromethanesulfonate and 2.76 g (20 mmol) of potassium carbonate are then added, and the mixture is stirred at room temperature with exclusion of light for a further 30 h. After removal of the dichloromethane in vacuo, the residue is chromatographed on basic aluminium oxide (activity grade 1) with THF and finally recrystallised from dichloromethane/methanol. Yield: 1.73 g, 47.4%; purity: >99.5% according to NMR.

Example 36

Synthesis of main-group metal complexes Tris(2-(2-oxyphenylmethyl)-6-pyridyl)fluoromethane aluminium

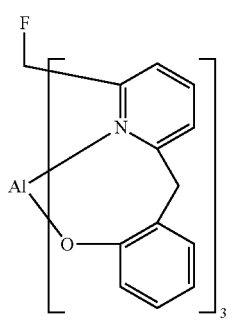

1.02 g (5 mmol) of aluminium triisopropoxide are added to a solution of 2.92 g (5 mmol) of tris(2-(2-hydroxyphenylmethyl)-6-pyridyl)fluoromethane in 100 ml of toluene, and the mixture is subsequently heated under reflux for 1 h. The solvent is then distilled off to about 10 ml, and 50 ml of n-heptane are added to the suspension. The solid is filtered off, washed with n-heptane and recrystallised from DMSO. Yield: 2.43 g, 80.0%; purity: >99.5% according to NMR.

The following compounds are prepared analogously starting from the corresponding ligand:

| Ex. | Starting material | Product | Yield |
|---|---|---|---|
| 37 | (Example 24) | Ga complex | 84.2% |
| 38 | (Example 24) | In complex | 71.2% |
| 39 | (Example 24) | La complex | 56.8% |

Production and Characterisation of Organic Electroluminescent Devices:

OLEDs are produced by the general process outlined below. This must of course be adapted in individual cases to the particular circumstances (for example layer-thickness variation in order to achieve optimum efficiency or colour).

General Process for the Production of OLEDs:

After the ITO-coated substrates (for example glass support, PET film) have been cut to the correct size, they are cleaned in a plurality of cleaning steps in an ultrasound bath (for example soap solution, Millipore water, isopropanol). They are dried by blowing with an $N_2$ gun and stored in a desiccator. Before vapour-coating with the organic layers, they are treated with an ozone plasma device for about 20 minutes. It may be advisable to use a polymeric hole-injection layer as the first organic layer. This is generally a conjugated, conductive polymer, such as, for example, a polyaniline derivative (PANI) or a polythiophene derivative (for example PEDOT, BAYTRON P™ from BAYER). This is then applied by spin coating. The organic layers are applied successively by vapour deposition in a high-vacuum unit. The layer thickness of the respective layer and the vapour-deposition rate are monitored and adjusted via a quartz resonator. It is also possible for individual layers to consist of more than one compound, i.e. in general a host material may be doped with a guest material. This is achieved by co-evaporation from two or more sources. An electrode is then applied to the organic layers. This is generally carried out by thermal evaporation (Balzer BA360 or Pfeiffer PL S 500). The transparent ITO electrode is subsequently contacted as anode and the metal electrode as cathode, and the device parameters are determined.

OLEDs having the following structure are produced analogously to the general process mentioned above:

PEDOT 20 nm (spin-coated from water; PEDOT purchased from BAYER AG; poly[3,4-ethylenedioxy-2,5-thiophene])

HIM1 20 nm of 2,2',7,7'-tetrakis(di-p-tolylamino)spiro-9,9'-bifluorene (vapour-deposited)

NPB 20 nm of 4,4'-bis(1-naphthylphenylamino)biphenyl (vapour-deposited)

mCP 20 nm of 1,3-bis(N-carbazolyl)benzene (vapour-deposited) doped with 10% of triplet emitter examples according to the invention see table BCP 8 nm of 2,9-dimethyl-4,7-diphenyl-1,10-phenanthroline (vapour-deposited)

AlQ$_3$ 20 nm (vapour-deposited)

L1/Al 5 nm of LiF, 150 nm of Al on top as cathode.

This as yet unoptimised OLED is characterised by standard methods. Table 1 shows the efficiency and voltage at 500 cd/m$^2$ and the colour.

TABLE 1

| Ex. | Emitter | Efficiency [cd/A] at 500 cd/m$^2$ | Voltage [V] at 500 cd/m$^2$ | Colour CIE x, y |
|---|---|---|---|---|
| 40 | Example 26 | 6.3 | 7.1 | 0.15/0.14 |
| 41 | Example 27 | 8.0 | 6.4 | 0.17/0.27 |
| 42 | Example 28 | 25.9 | 6.0 | 0.48/0.44 |
| 43 | Example 30 | 5.9 | 6.9 | 0.15/0.16 |
| 44 | Example 32 | 4.8 | 6.3 | 0.15/0.17 |
| 45 | Example 33 | 5.9 | 6.7 | 0.15/0.17 |
| 46 | Example 34 | 9.2 | 5.9 | 0.15/0.16 |
| 47 | Example 35 | 15.3 | 7.2 | 0.22/0.38 |

The invention claimed is:

1. A compound of the formula (1)

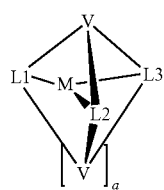

formula (1)

containing a metal M coordinated to a ligand L of the formula (2) and M is a transition metal, aluminium or gallium,

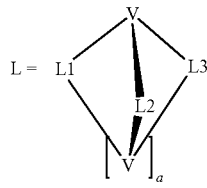

formula (2)

wherein the following applies to the symbols and indices used:

V is B, BR$^-$, CR, CO$^-$, CN(R$^1$)$_2$, SiR, N, NO, NR$^+$, P or PO;

a is 0 or 1, where, in the case where a=0, the bridging unit V is not present;

L1 is a ligand moiety of the formula (3)

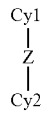

formula (3)

L2 and L3 are, identically or differently on each occurrence, each a ligand moiety of the formula (3), formula (4) or formula (5)

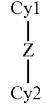

formula (3)

formula (4)

formula (5)

Cy1 and Cy2 are, identically or differently on each occurrence, an aryl or heteroaryl group having 5 to 30 aromatic ring atoms, which is optionally substituted by one or more radicals R, or a cyclic saturated or preferably unsaturated carbene; one of the two groups Cy1 or Cy2 here is bonded to the metal via a formally negatively charged carbon or via a formally negatively charged exocyclic donor atom, and the other of the two groups Cy1 and Cy2 is bonded via a neutral donor atom which is part of the group Cy1 or Cy2 and which is selected from nitrogen, and carbon in the form of a carbene;

Z is, identically or differently on each occurrence, O, S, S(=O), S(=O)$_2$, NR, PR, P(=O)R, C(=O), SiR$_2$ or BR;

R is on each occurrence, identically or differently, H, D, F, Cl, Br, I, N(R$^1$)$_2$, CN, Si(R$^1$)$_3$, B(OR$^1$)$_2$, C(=O)R$^1$, P(=O)(R$^1$)$_2$, a straight-chain alkyl, alkenyl, alkynyl, or alkoxy group having 1 to 40 C atoms or a branched or cyclic alkyl, alkenyl, alkynyl, or alkoxy group having 3 to 40 C atoms, each of which is optionally substituted by one or more radicals R$^1$, where one or more non-adjacent CH$_2$ groups is optionally replaced by R$^1$C=CR$^1$, C≡C, Si(R$^1$)$_2$, NR$^1$ or O, and where one or more H atoms is optionally replaced by F, or an aromatic or heteroaromatic ring system having 5 to 60 aromatic ring atoms, which optionally in each case be substituted by one or more radicals $R^1$, or an aryloxy or heteroaryloxy group having 5 to 60 aromatic ring atoms, which is optionally substituted by one or more radicals $R^1$, or a diarylamino group, diheteroarylamino group or arylheteroarylamino group having 10 to 40 aromatic ring atoms, which may be substituted by one or more radicals $R^1$, or a combination of these systems; two or more substituents R here optionally forms a mono- or polycyclic aliphatic, aromatic and/or benzo-fused ring system with one another;

D1 and D2 are identical or different on each occurrence and which contain at least nitrogen, phosphorus, oxygen or sulfur.

2. The compound according to claim 1, wherein the ligand L has a structure of the formula (6), (7), (8), (9) or (10), where the symbols and indices used have the meanings mentioned in claim 1:

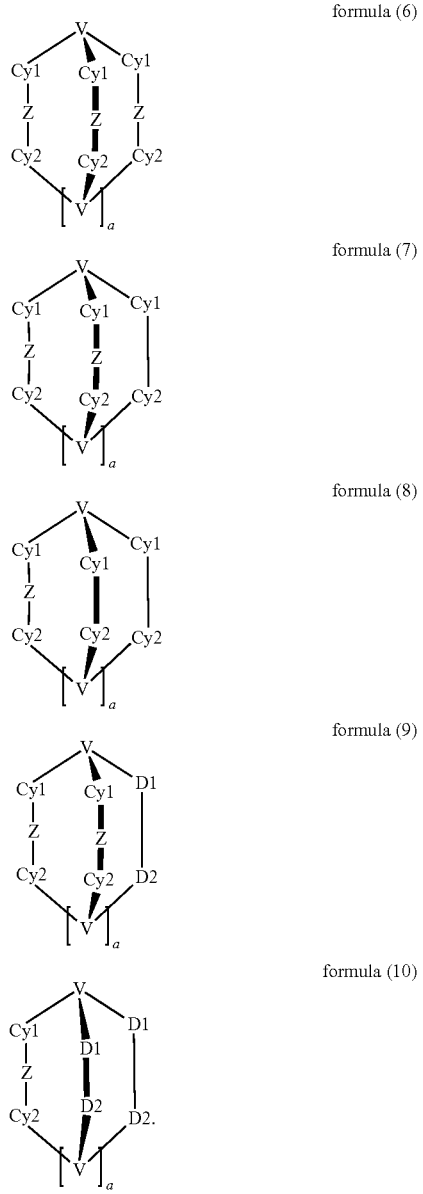

3. The compound according to claim 1, wherein M is tungsten, rhenium, ruthenium, osmium, rhodium, iridium, platinum, gold, scandium, yttrium, lanthanum, aluminium, gallium or indium.

4. The compound according to claim 1, wherein Z on each occurrence, identically or differently, and is O, S, NR or C(=O).

5. The compound according to claim 1, wherein the ligand moieties of the formula (5) are selected from substituted or unsubstituted β-ketoketonates, β-ketoesters, β-diesters, carboxylates derived from aminocarboxylic acids, iminoacetoacetonates, hydroxamates, pyridylphosphines, α-phosphinocarboxylates, glycol ethers, ether alcoholates, dialcoholates derived from dialcohols, dithiolates derived from dithiols, diamines, imines, diimines, diphosphines and salicyliminates derived from salicylimines.

6. A process for the preparation of the compound according to claim 1 which comprises reacting the ligands of the formula (2) or precursors of these ligands with metal alkoxides of the formula (47), with metal ketoketonates of the formula (48) or with metal halides of the formula (49)

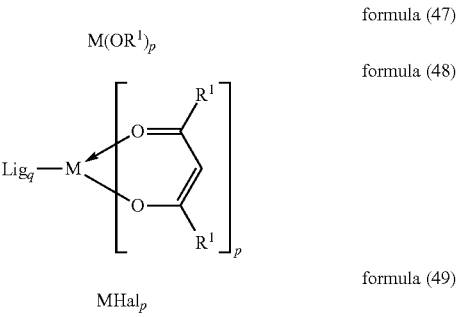

where M and $R^1$ have the same meaning as described above, and the following applies to the other symbols and indices:

Hal is on each occurrence, identically or differently, F, Cl, Br or I;

Lig is on each occurrence, identically or differently, a neutral or monoanionic, monodentate or bidentate ligand, for example a halide or hydroxide;

p is on each occurrence, identically or differently, 1, 2, 3, 4 or 5, where p in formulae (47) and (49) indicates the valency of the metal M;

q is on each occurrence, identically or differently, 0, 1, 2, 3 or 4;

the compound of the formula (48) here is optionally charged and optionally contains a counterion.

7. The process as claimed in claim 6, wherein q is 0, 1 or 2.

8. An oligomer, polymer or dendrimer comprising one or more compounds according to claim 1, in which one or more bonds are present from the complex of the formula (1) to the polymer, oligomer or dendrimer.

9. An electronic component comprising the compounds according to claim 1.

10. The electronic component as claimed in claim 9, wherein the electronic component is an organic integrated circuit (O-IC), an organic field-effect transistors (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser), an organic electroluminescent device (OLED, PLED).

11. An organic electroluminescent device which comprises an emitting layer which comprises the compound according to claim 1.

12. An organic electroluminescent device which comprises an emitting layer which comprises the compound according to claim 1 in combination with a matrix material, employed as matrix material for an emitting compound in an emitting layer, employed as hole-blocking material in a hole-blocking layer or as electron-transport material in an electron-transport layer.

13. An organic electroluminescent device which comprises an emitting layer which comprises the compound according to claim 1 is employed as matrix material for a phosphorescent compound.

14. A compound of the following applies to the ligand moiety L1 thereof together with the metal and the bridging unit V of the formula (11):

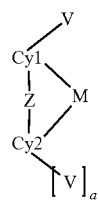

formula (11)

M is a transition metal, aluminium or gallium;
Cy1 and Cy2 are, identically or differently on each occurrence, an aryl or heteroaryl group having 5 to 30 aromatic ring atoms, which is optionally substituted by one or more radicals R, or a cyclic saturated or preferably unsaturated carbene; one of the two groups Cy1 or Cy2 here is bonded to the metal via a formally negatively charged carbon or via a formally negatively charged exocyclic donor atom, and the other of the two groups Cy1 and Cy2 is bonded via a neutral donor atom which is part of the group Cy or Cy2 and which is selected from nitrogen, and carbon in the form of a carbene;
V is B, BR$^-$, CR, CO$^-$, CN(R$^1$)$_2$, SiR, N, NO, NR$^+$, P or PO;
where U stands for N, P, P(=O), CR or SiR, and the dashed bonds each represent the bonds to the ligand moieties;
Z is, identically or differently on each occurrence, O, S, S(=O), S(=O)$_2$, NR, PR, P(=O)R, C(=O), SiR$_2$ or BR;
R is on each occurrence, identically or differently, H, D, F, Cl, Br, I, N(R$^1$)$_2$, CN, Si(R$^1$)$_3$, B(OR$^1$)$_2$, C(=O)R$^1$, P(=O)(R$^1$)$_2$, a straight-chain alkyl, alkenyl, alkynyl, or alkoxy group having 1 to 40 C atoms or a branched or cyclic alkyl, alkenyl, alkynyl, or alkoxy group having 3 to 40 C atoms, each of which is optionally substituted by one or more radicals R$^1$, where one or more non-adjacent CH$_2$ groups is optionally replaced by R$^1$C=CR$^1$, C≡C, Si(R$^1$)$_2$, NR$^1$ or O, and where one or more H atoms is optionally replaced by F, or an aromatic or heteroaromatic ring system having 5 to 60 aromatic ring atoms, which optionally in each case be substituted by one or more radicals R$^1$, or an aryloxy or heteroaryloxy group having 5 to 60 aromatic ring atoms, which is optionally substituted by one or more radicals R$^1$, or a diarylamino group, diheteroarylamino group or arylheteroarylamino group having 10 to 40 aromatic ring atoms, which may be substituted by one or more radicals R$^1$, or a combination of these systems; two or more substituents R here optionally forms a mono- or polycyclic aliphatic, aromatic and/or benzo-fused ring system with one another;
R$^1$ is on each occurrence, identically or differently, H, F or an aliphatic, aromatic and/or heteroaromatic hydrocarbon radical having 1 to 20 C atoms, in which, in addition, one or more H atoms is optionally replaced by F; two or more substituents R$^1$ here optionally forms a mono- or polycyclic aliphatic or aromatic ring system with one another; and
a is 0 or 1, where, in the case where a=0, the bridging unit V is not present.

15. The compound according to claim 14, wherein the ligand moiety L1, together with the metal and the bridging unit V, has a structure of the formulae (15) to (30):

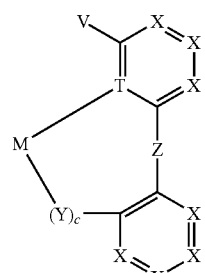

formula (15)

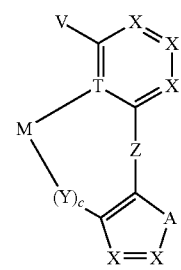

formula (16)

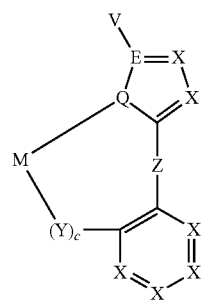

formula (17)

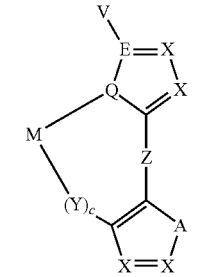

formula (18)

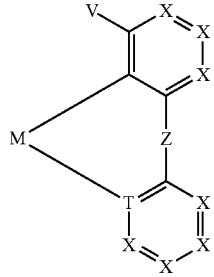

formula (19)

formula (20)
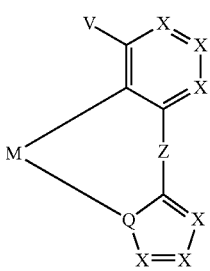
formula (21)
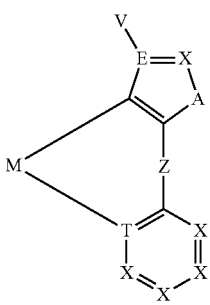
formula (22)
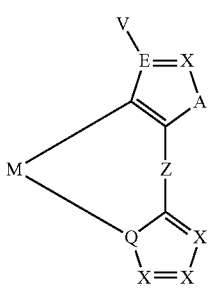
formula (23)
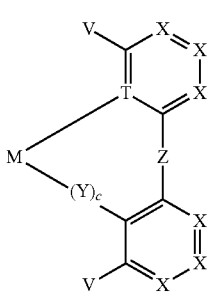
formula (24)
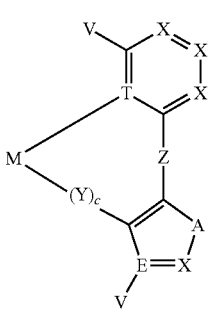
formula (25)
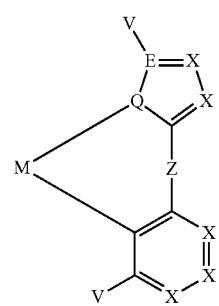
formula (26)
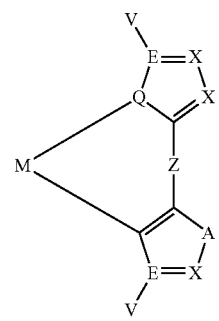
formula (27)
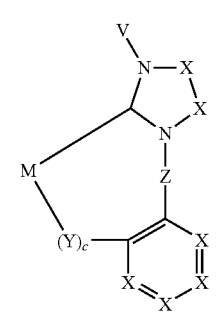
formula (28)
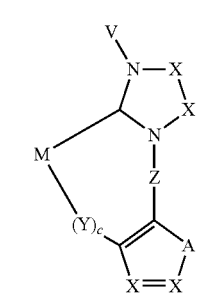
formula (29)
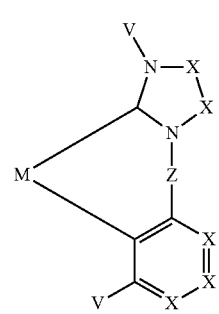

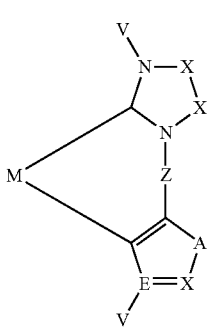

formula (30)

wherein M, Z, and R are the same as defined in formula (11)

V is B, BR⁻, CR, CO⁻, CN(R¹)₂, SiR, N, NO, NR⁺, P or PO;

where U stands for N, P, P(=O), CR or SiR, and the dashed bonds each represent the bonds to the ligand moieties;

R¹ is on each occurrence, identically or differently, H, F or an aliphatic, aromatic and/or heteroaromatic hydrocarbon radical having 1 to 20 C atoms, in which, in addition, one or more H atoms is optionally replaced by F; two or more substituents R¹ here optionally forms a mono- or polycyclic aliphatic or aromatic ring system with one another;

E is, identically or differently on each occurrence, C or N;

Q is, identically or differently on each occurrence, O, S, or N;

T is, identically or differently on each occurrence, N or C;

A is, identically or differently on each occurrence, NR¹, S or O;

X is, identically or differently on each occurrence, CR or N where in this case a double bond is present between the two groups X in the carbene ring in the formulae (27), (28), (29) and (30); or X in the carbene ring in the formulae (27), (28), (29) and (30) stands, identically or differently on each occurrence, for CR₂;

Y is, identically or differently on each occurrence, NR¹, COO⁻, O or S;

c is, identically or differently on each occurrence, 0 or 1.

* * * * *